(12) United States Patent
Dickinson

(10) Patent No.: US 9,689,867 B2
(45) Date of Patent: *Jun. 27, 2017

(54) ASSAYS FOR AFFINITY PROFILING OF NUCLEIC ACID BINDING PROTEINS

(71) Applicant: Affymetrix, Inc., Santa Clara, CA (US)

(72) Inventor: Philip Dickinson, Cupertino, CA (US)

(73) Assignee: Affymetrix, Inc., Santa Clara, CA (US)

( * ) Notice: Subject to any disclaimer, the term of this patent is extended or adjusted under 35 U.S.C. 154(b) by 196 days.

This patent is subject to a terminal disclaimer.

(21) Appl. No.: 14/566,029

(22) Filed: Dec. 10, 2014

(65) Prior Publication Data

US 2015/0160202 A1    Jun. 11, 2015

Related U.S. Application Data

(63) Continuation of application No. 13/543,711, filed on Jul. 6, 2012, now Pat. No. 8,932,819.

(60) Provisional application No. 61/505,019, filed on Jul. 6, 2011.

(51) Int. Cl.
*G01N 33/53* (2006.01)
*C12Q 1/68* (2006.01)

(52) U.S. Cl.
CPC ....... *G01N 33/5308* (2013.01); *C12Q 1/6806* (2013.01); *C12Q 1/6827* (2013.01); *C12Q 1/6837* (2013.01); *C12Q 1/6811* (2013.01)

(58) Field of Classification Search
None
See application file for complete search history.

(56) References Cited

U.S. PATENT DOCUMENTS

| | | | |
|---|---|---|---|
| 6,949,638 B2 | 9/2005 | Mittmann et al. | |
| 7,351,528 B2 | 4/2008 | Landegren | |
| 8,932,819 B2 * | 1/2015 | Dickinson | C12Q 1/6806 435/6.11 |

OTHER PUBLICATIONS

Bulyk (2007) "Protein Binding Microarrays for the Characterization of Protein-DNA Interactions." *Advances Biochemical Engineering Biotechnology,* 104: 65-85.

Grant et al. (2006) "Variant of Transcription factor 7-like 2 (TCF7L2) gene confer risk of type 2 diabetes." *Nature Genetics,* 38(3): 320-323.

Hardenbol et al. (2003) "Multiplexed genotyping with sequence-tagged molecular inversion probes." *Nature Biotechnology,* 21(6): 673-678.

Horak and Snyder (2002) "ChIP-chip: A Genomic Approach for Identifying Transcription Factor Binding Sites." *Methods in Enzymology,* 350: 469-483.

Kasowski et al. (2010) "Variation in Transcription Factor Binding Among Humans." *Science,* 328: 232-235.

Mukherjee et al. (2004) Rapid analysis of the DNA-binding specificities of transcription factors with DNA microarray. *Nature Genetics,* 36(12): 1331-1339.

Yan and Marriott (2003) "Analysis of protein interaction using fluorescence technologies." *Current Opinion in Chemical Biology,* 7: 635-640.

Zheng et al. (2010) "Genetic Analysis of Variation in Transcription Factor Binding in Yeast." *Nature,* 464(7292): 1187-1191.

\* cited by examiner

*Primary Examiner* — James Martinell
(74) *Attorney, Agent, or Firm* — Quine Intellectual Property Law Group P.C.

(57) ABSTRACT

Methods, compositions and kits are disclosed for assays to determine the binding affinity of DNA-binding proteins or RNA-binding proteins for their corresponding recognition site(s). In particular, assays are disclosed for measuring binding affinities when either the binding protein, or the recognition sequence of the recognition site, or cofactor proteins, contain one or more mutations. The disclosed assays can thus be utilized to measure the effect on transcription factor binding caused by mutations within the recognition site, or mutations within the binding domain of the protein, and to provide binding affinity information that can be correlated with altered gene regulation and expression. The disclosed assays can be personalized to a specific person or organism, with the measured binding affinities based upon an individual's specific binding proteins and recognition sites. Furthermore, embodiments are capable of measuring binding affinities between multiple binding proteins and multiple recognition sites through an entirely in vitro process.

15 Claims, 9 Drawing Sheets

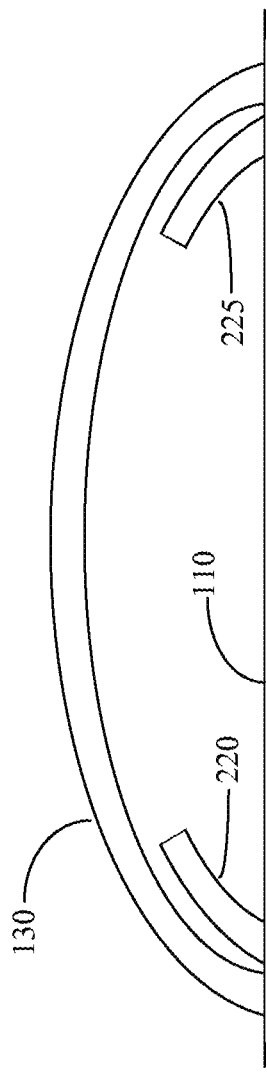
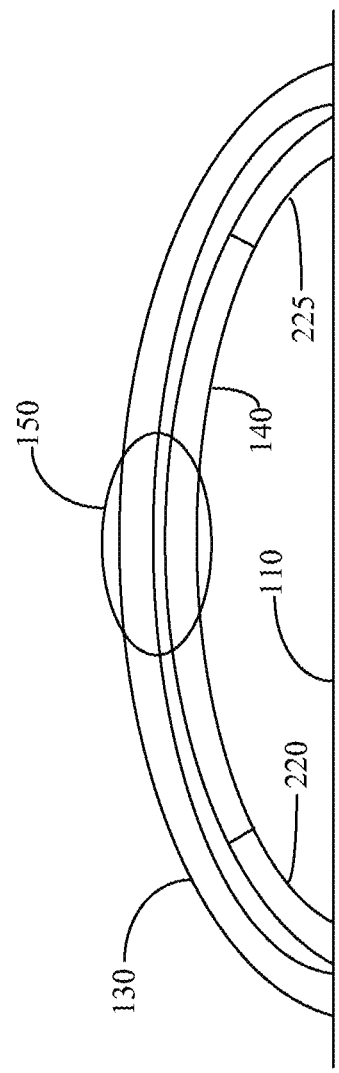

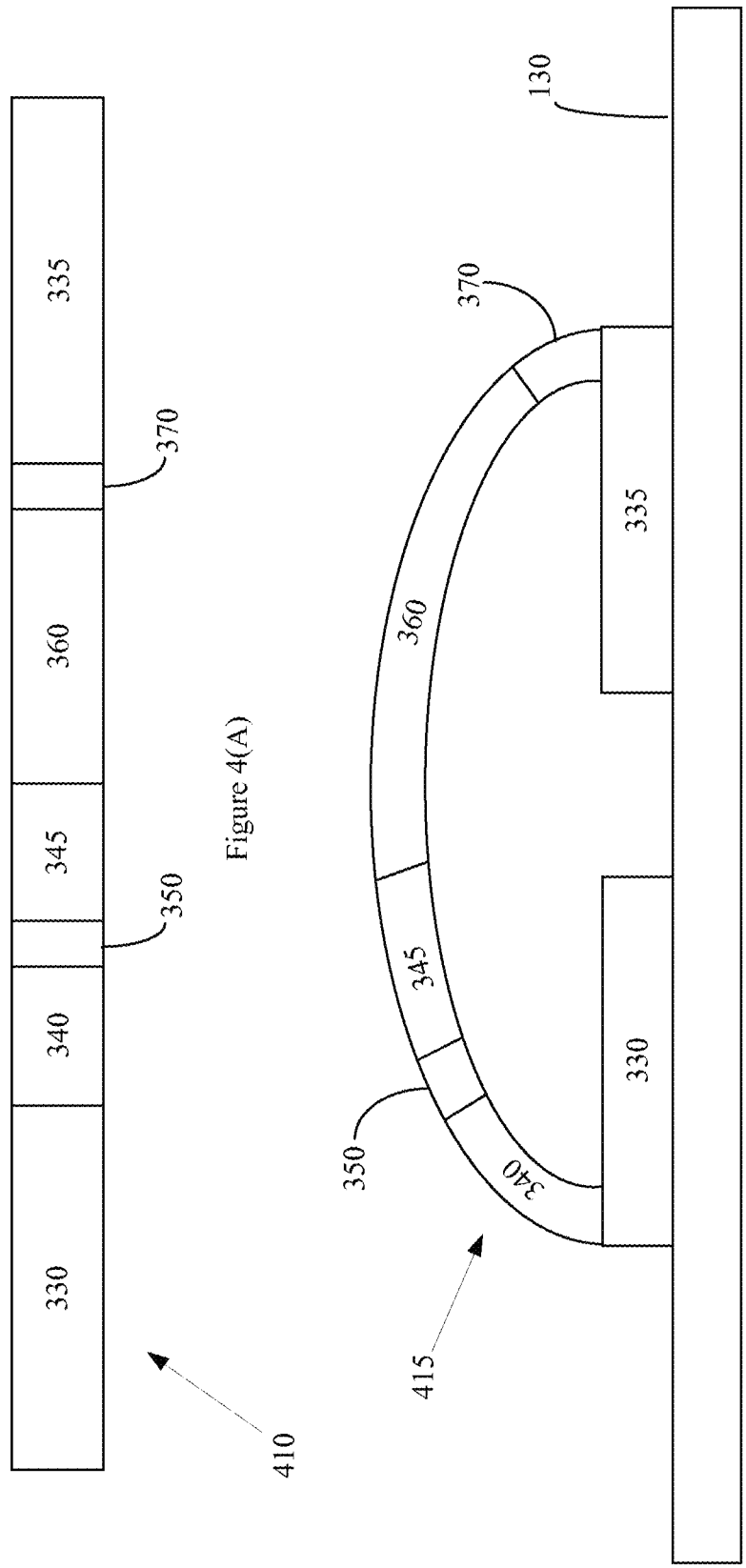

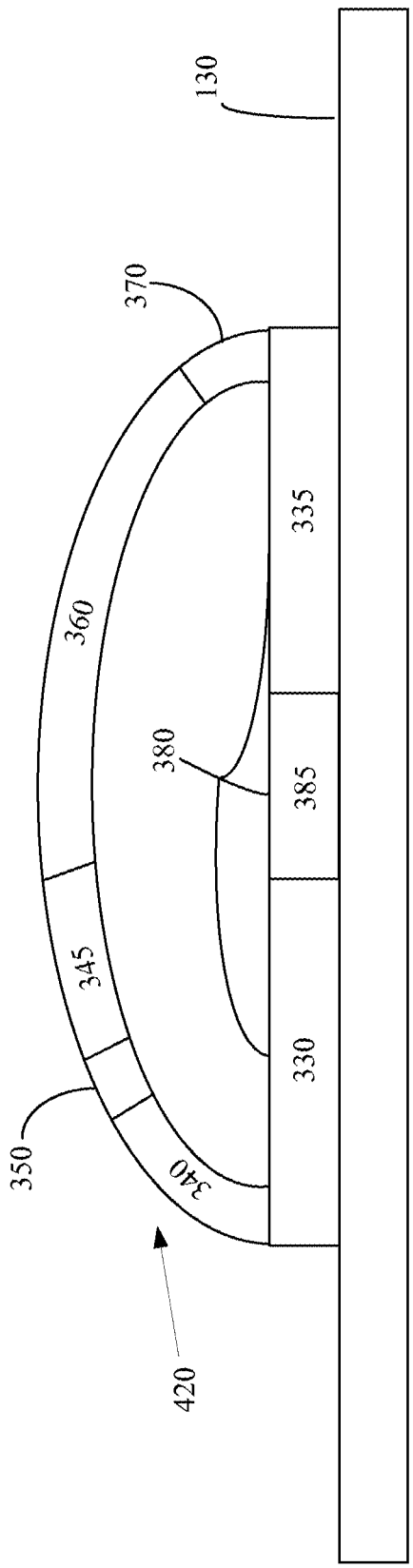
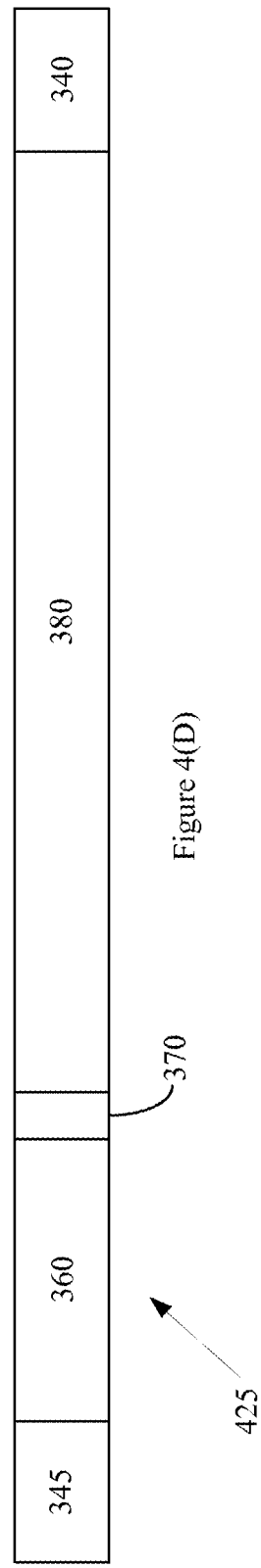
Figure 4(C)
Figure 4(D)

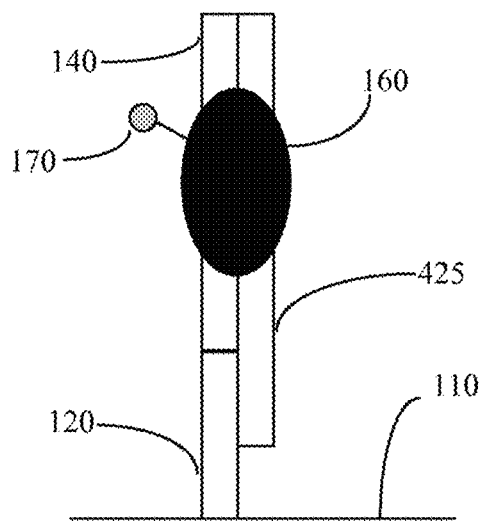
Figure 5(C')

ASSAYS FOR AFFINITY PROFILING OF NUCLEIC ACID BINDING PROTEINS

CROSS-REFERENCE TO RELATED APPLICATIONS

This application is a Continuation Application claiming priority and benefit of parent Utility Application "Assays for Affinity Profiling of Nucleic Acid Binding Proteins", by Philip Dickinson, Ser. No. 13/543,711, filed Jul. 6, 2012, which claims priority to and benefit of a prior U.S. Provisional Application No. 61/505,019, filed Jul. 6, 2011. The full disclosure of the prior applications are incorporated herein by reference

FIELD OF THE INVENTION

The presently disclosed methods and kits are related to assays for measuring the binding affinity of DNA-binding proteins or RNA-binding proteins for their corresponding recognition site(s). Specifically, assays are disclosed for measuring the binding affinity of a DNA-binding or RNA-binding domain of a binding protein, such as a transcription factor, for a recognition site within a nucleic acid. Depending upon the assay, the recognition sequence of the recognition site at issue may contain one or more mutations, such as SNPs, that affect the binding affinity of the relevant binding protein(s). The disclosed assays are capable of measuring binding affinities based upon a specific person or organism's binding proteins and recognition sites, thus enabling correlation of mutations affecting binding affinities with their corresponding changes, such as changes within gene expression and regulation that affect the diagnosis and/or treatment of various diseases and conditions.

BACKGROUND OF THE INVENTION

Nucleic acid binding proteins, namely DNA-binding proteins and RNA-binding proteins, are proteins that bind to either deoxyribonucleic acid (DNA) or ribonucleic acid (RNA). The binding can be non-specific, specific for a particular recognition site, or specific for a plurality of recognition sites, with recognition sites consisting of a specific recognition sequence of DNA or RNA. Examples of DNA-binding proteins are transcription factors, polymerases, nucleases, and histones. These proteins perform such functions as regulating transcription, cleaving DNA, and packing DNA into nucleosomes. Variation in these functions, such as the regulation of transcription by transcription factors, is believed to be responsible for many genetic differences between individuals that lead to phenotypic differences. (See, e.g., Kasowski et al., "Variation in Transcription Factor Binding Among Humans," Science, 328: 232-235 (2010); and Zheng et al., "Genetic analysis of variation in transcription factor binding in yeast," Nature, 464: 1187-1191 (2010)). Examples of RNA-binding proteins are translation initiation factors that bind with messenger RNA (mRNA), small nuclear ribonucleoproteins (snRNPs), and RNA editing proteins such as RNA specific adenosine deaminase. These RNA binding proteins perform such functions as regulating translation and RNA splicing and editing. Additionally, studies have shown that mutations such as single-nucleotide polymorphisms (SNPs), insertions, and deletions among either the recognition sequences or the genes which encode binding proteins can cause significant phenotypic changes. (See, e.g., Kasowski et al., Science, 328: 232-235 (2010); Zheng et al., Nature, 464: 1187-1191 (2010); and Grant et al., "Variant of transcription factor 7-like 2 (TCF7L2) gene confers risk of type 2 diabetes," Nature Genetics, 38(3): 320-323 (2006)).

Previous assay methods to measure the binding affinity between a binding protein and its corresponding recognition site include chromatin immunoprecipitation with subsequent analysis by microarrays or sequencing, protein binding microarrays, and related techniques using surface plasmon resonance that followed early techniques to studying DNA-protein interactions such as DNA footprinting assays. (See, e.g., Galas and Schmitz, "DNAase footprinting: a simple method for the detection of protein-DNA binding specificity," Nucleic Acids Research, 5(9): 3157-3170 (1978)). Approaches using chromatin immunoprecipitation with microarrays generally follow a protocol of fixing protein-nucleic acid complexes in vivo, such as with formaldehyde, lysing the cells, fragmenting the DNA, such as through sonication, immunoprecipitating the binding proteins of interest, extracting and purifying the associated nucleic acid fragments, and detecting these fragments with the array. (See, e.g., Horak and Snyder, "ChIP-chip: A Genomic Approach for Identifying Transcription Factor Binding Sites," Methods in Enzymology, 350: 469-483 (2002)). Disadvantages of this technique include the requirement of specific antibodies for each binding protein of interest, and in addition to the added complexity and cost of such a requirement, there are binding proteins for which an antibody may not be available, or for which the conditions and time points enabling the antibody's expression and activity are unknown. (See, e.g., Mukherjee et al., "Rapid analysis of the DNA-binding specificities of transcription factors with DNA microarrays," Nature Genetics, 36(12): 1331-1339 (2004)). Alternative chromatin immunoprecipitation techniques utilize subsequent sequencing in place of microarrays to identify the sequences that are bound by the binding proteins. (See, e.g., Robertson et al., "Genome-wide profiles of STAT1 DNA association using chromatin immunoprecipitation and massively parallel sequencing," Nature Methods, 4(8): 651-657 (2007)). However, specific antibodies must still be procured regardless of the change in the subsequent mode of analysis, and both techniques are also dependent upon the in vivo component of fixing binding protein-nucleic acid complexes, thus complicating the process of analyzing particular binding proteins and/or recognition sites of interest to a researcher or clinician.

Protein binding microarrays allow the entire assay to be performed in vitro, and require the production of a double-stranded nucleic acid array, such as a spotted double-stranded DNA array. (See, Mukherjee et al., Nature Genetics, 36(12): 1331-1339 (2004)). Binding proteins of interest are then introduced to the array with subsequent detection of the bound binding proteins. Such arrays, however, are limited to using the exact recognition sites within the double-stranded sequences spotted or otherwise produced upon the array. Mutations within recognition sequences such as SNPs, insertions, deletions, inversions, or a combination thereof, can drastically affect the binding affinity that a particular binding protein will have with that mutated recognition site. This can be especially important with regard to binding proteins which bind to multiple sequences, as these binding proteins will not be specific to only one recognition site, and additional changes to the recognition sequence of a possible recognition site through one or more mutations can substantially alter, among other process, regulation mechanisms employing competitive binding among multiple nucleic acid binding proteins. (See, e.g., Wang, "Finding Primary Targets of Transcriptional Regulators," Cell Cycle, 4(3): 356-357 (2005); and Bulyk, "Protein Binding Microarrays for the Characterization of Protein-DNA Interactions," Advances in Biochemical Engineering Biotechnology, 104: 65-85 (2007)). Furthermore, while related assays utilizing surface plasmon resonance can provide quantitative kinetic data, such assays are not easily scalable. (See, e.g., Bulyk, Advances in Biochemical Engineering Biotechnology, 104: 65-85 (2007); and Mukherjee et al., Nature Genetics, 36(12): 1331-1339 (2004)).

Additionally, some binding proteins operate in association with other molecules within their overall binding mechanism in various conditions. For example, transcription elongation factors GreA and GreB bind with and induce nucleolytic activity in RNA polymerase. (See, Laptenko et al., "Transcript cleavage factors GreA and GreB act as transient catalytic components of RNA polymerase," The EMBO Journal, 22: 6322-6334 (2003)). Many DNA-binding proteins function in concert with cofactors as well, such as Mcm1 of the MADS box family of transcription factors, which bind with high specificity and affinity to their corresponding recognition sites but that require interaction with different cofactors such as α1 or Ste12. (See, Mead et al., "Interactions of the Mcm1 MADS Box Protein with Cofactors That Regulate Mating in Yeast," Molecular and Cellular Biology, 22(13): 4607-4621 (2002)). Non-protein molecules may also affect the interaction of a binding protein with a recognition sequence, such as miRNAs or siRNAs and their affect on the binding affinities of RNA-binding proteins. (See, Jacobsen et al., "Signatures of RNA binding proteins globally coupled to effective microRNA target sites," Genome Research, 20: 1010-1019 (2010)). Thus, mutations that affect the interaction between a binding protein and its accessory molecules, such as cofactor proteins or miRNAs, can directly affect binding affinities through, for instance, changes in certain residues which are crucial for proper interaction of a binding protein with its cofactors. (See, Mead et al., Molecular and Cellular Biology, 22(13): 4607-4621 (2002)).

Therefore, these previous methods fail to meet the ongoing need to personalize diagnostic and treatment options for individual patients in straightforward and cost-effective manner, and also fail to enable research of binding affinities of interest that accounts for possible mutations within a recognition sequence, including mutations that are rare and/or previously unknown. In addition to the continuing need for improved methods to measure the binding affinity of binding proteins for various recognition sites, there is also a need for improved methods to measure the differences effected in binding affinities when either the sequence of the gene encoding the binding protein, or the recognition sequence of the recognition site, or both, possess one or more mutations. As discussed above, mutations which affect the binding affinity of a binding protein can cause significant phenotypic changes. For example, the presence of SNPs can alter binding affinities sufficiently to cause corresponding differences in gene expression, thus effecting a functional genetic variation. (See, e.g., Kasowski et al., Science, 328: 232-235 (2010); Zheng et al., Nature, 464: 1187-1191 (2010); and Grant et al., Nature Genetics, 38(3): 320-323 (2006)). Assays to detect and measure these binding affinity changes are useful in diagnosing and treating conditions, such as SNPs within transcription factor 7-like 2 (TCF7L2) being correlated with an increased risk for type 2 diabetes. (See, e.g., Grant et al., Nature Genetics, 38(3): 320-323 (2006)). Likewise, mutations in the recognition sequence of binding proteins have also been shown to be associated with diseases and disorders, such as a SNP within the promoter of human coagulation factor VII leading to an inability of Specificity Protein 1 (Sp1) to bind, which results in a severe bleeding disorder. (See, Carew et al., "Severe Factor VII Deficiency Due to a Mutation Disrupting an Sp1 Binding Site in the Factor VII Promoter," Blood, 92: 1639-1645 (1998)). Thus, in the continuing quest to personalize medical diagnostics and therapies to the specific individual being treated, there is a need for improved methods to measure the binding affinities of binding proteins based upon the individual's personal genome so that diagnoses and therapies can be adjusted accordingly. Analysis of an individual's particular binding affinities between various binding proteins and their relevant recognition sites can further explain the genetic contribution to a variety of medical conditions when knowledge of the mutation alone is insufficient to determine and implement a therapy that is personalized to the individual.

BRIEF SUMMARY OF THE INVENTION

Various embodiments of the disclosed assay fulfill the need for improved assays to measure the affinity of binding proteins for their recognition sites, particularly the need for assays which are personalized to an individual, including some embodiments which incorporate both nucleic acid sequences and binding proteins specific to the individual of interest. In general, the disclosed methods and kits are directed to measuring an affinity level of at least one binding protein for at least one recognition site.

Certain embodiments begin with a capture oligonucleotide attached to a substrate, where the capture oligonucleotide includes a portion that is complementary to a target nucleic acid sequence. Capture oligonucleotides may be DNA or RNA, or analogs thereof, and of various sequence lengths depending upon the embodiment, including ranges from 10 to 100 nucleotides, and attached to the substrate at either their 5' or 3' end. Capture oligonucleotides may synthesized in situ on the substrate or may be attached to the substrate after synthesis. The substrate and array can be in any suitable format, including spotted and in situ synthesized microarrays, liquid arrays, inkjet arrays, and bead arrays. The portion of the capture oligonucleotides that is complementary to the target nucleic acid sequence will vary in length depending upon the desired characteristics of the assay and the technique utilized to create the capture oligonucleotides. The target nucleic acid sequence may be from any organism of interest, eukaryotic or prokaryotic, including a human individual such as a patient. Utilization of a specific individual to provide the genetic material upon which the target sequence is extracted or based upon allows customization of the target sequences within the assay to include whatever mutations, such as SNPS, that may be present in the source individual. Various processing and preparation techniques of the sample and the target sequences may be utilized according to different embodiments. When the target sequences are in a suitable condition for hybridization, they are introduced to the substrate and allowed to hybridize with the capture oligonucleotides present.

Certain embodiments will then synthesize a strand that is complementary to the target sequence. In some embodiments, this may occur enzymatically through extension of the capture oligonucleotide with a polymerase until a double-stranded oligonucleotide is formed with the target sequence and the extended capture oligonucleotide. Other embodiments will not create or retain double-stranded oligonucleotides, as certain nucleic acid binding proteins are specific to single-stranded DNA or RNA. Whether the resulting oligonucleotide is double-stranded or single-stranded, it desirably includes a recognition site, comprising a recognition sequence, for a binding protein. The identity and length of the recognition sequence will depend upon the particular binding protein of interest.

Embodiments will then introduce one or more binding proteins and allow them to potentially bind to the one or more recognition sites which may be present. Multiple binding proteins may be utilized within an assay, such as a wild type binding protein and one or more mutant variants. Binding proteins may be obtained from commercial sources, or preferentially translated based upon the genetic material of the individual of interest, such as through in vitro recombinant translation. Within certain embodiments, the binding proteins at issue may require or desirably involve activation, modification, etc. before the assay continues. Such adjustments to the binding proteins may include, e.g., phosphorylation, acetylation or methylation, depending on the particular binding protein of interest.

Translation and use of binding proteins specific to the individual of interest allows any mutations present in the binding protein to be accounted for within the assay. Embodiments which utilize genetic material from an individual of interest to obtain or produce the target nucleic acid sequences and binding proteins to be utilized within the assay produce binding affinity measurements which are entirely specific to the individual of interest. The binding proteins may be either directly or indirectly labeled, such as with fluorescent labels. Antibodies may also be utilized within the labeling strategy in some embodiments. In some embodiments, each different type of binding protein may have a distinguishable label or combination of labels. Detection of the relevant labels allows the assay to measure the affinity level of the one or more binding proteins of interest for one or more recognition sites of interest. The measured affinity level may be in terms of absolute and/or relative quantification, depending on the label(s) utilized, the configuration of the assay, the manner of detection (e.g., excitation and observation of fluorescent emissions from different fluorophores), etc.

In certain embodiments, the assay includes capture oligonucleotides in which the complementary portion, which hybridizes with the target nucleic acid sequence, is a unique sequence. In other embodiments, the complementary portion is a unique, conserved sequence. The capture oligonucleotide may also include additional portions, such as an identification portion comprising a unique sequence. Depending upon the embodiment, one or more substrates may be utilized within a single assay, and each substrate may have one or more capture oligonucleotides. Each substrate may have attached only a single type of capture oligonucleotide, or may have multiple different capture oligonucleotides attached. In certain embodiments, a pair of capture oligonucleotides may be utilized for each target nucleic acid sequence, where each of the two capture oligonucleotides hybridizes to a different portion of the target nucleic acid sequence. The substrate itself may also comprise additional components, such as detectable, pre-determined code built into the substrate that allows a particular substrate to be distinguished from other substrates that may be used within the same assay.

Certain embodiments incorporate the use of Molecular Inversion Probe (MIP) technology upstream of the binding protein affinity portion of the assay. MIP probes comprise at least two regions for cooperative hybridization with a target that facilitates circularization of the probe after hybridization, as well as other portions utilized within various embodiments for functionalities such as cleavage of the circularized probe, amplification through the use of primer binding sites, and the incorporation of unique tag sequences within amplicons. Various embodiments utilize MIP probes to selective enrich a nucleic acid sample for specific targets, while using the cooperative hybridization aspect of the probes to ensure high specificity while allowing for any mutations present within the recognition sequences of the recognition sites at issue to be incorporated within the amplicons. MIP probes enable many embodiments to carefully select the recognition sites from precise locations within the genome to ensure that the binding protein affinity portion of the assay is performed with respect to the recognition site of interest, and not with respect to a difference occurrence of the relevant recognition sequence within the sample.

The above embodiments are not necessarily inclusive or exclusive of each other and may be combined in any manner that is non-conflicting and otherwise possible, whether they be presented in association with a same, or a different, aspect or embodiment. The description of one embodiment is not generally intended to be limiting with respect to other embodiments. Also, any one or more function, step, operation, or technique described elsewhere in this specification may, in alternative embodiments, be combined with any one or more function, step, operation, or technique described in the summary. Thus, the above embodiments are illustrative rather than limiting.

BRIEF DESCRIPTION OF THE DRAWINGS

The above and further features will be more clearly appreciated from the following detailed description when taken in conjunction with the accompanying drawings. In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

FIG. 2(A) illustrates a non-limiting example of cooperative capture of a target fragment with two different capture oligonucleotides that are attached to a solid support.

FIG. 2(B) illustrates a non-limiting example of extension of one of the capture oligonucleotides based upon the target fragment captured in FIG. 2(A), thus forming a double-stranded protein binding site.

FIG. 4(A) illustrates a non-limiting example of a MIP probe in an initial, linear form.

FIG. 4(B) illustrates a non-limiting example of the MIP probe from FIG. 4(A) after cooperative hybridization of its two different genomic homology regions to a target nucleic acid.

FIG. 4(C) illustrates a non-limiting example of the MIP probe from FIG. 4(B) in circularized form after filling of the gap between the two genomic homology regions to form a single, combined genomic homology region.

FIG. 4(D) illustrates a non-limiting example of the MIP probe from FIG. 4(C) after linearization effected by separation of the MIP probe from the target nucleic acid and cleavage of the circularized MIP probe for re-linearization.

FIG. 5(A)-5(C) are non-limiting schematic diagrams showing an example of linearized MIP probes in a binding protein affinity assay. In FIG. 5(A), a MIP probe is hybridized with a capture oligonucleotide on a substrate. In FIG. 5(B), nucleic acid extension has generated a complementary fragment providing a double-stranded recognition site. In FIG. 5(C), a labeled binding protein specifically binds to the recognition site where it can be detected.

DETAILED DESCRIPTION

I. General Description

Figure 1A:
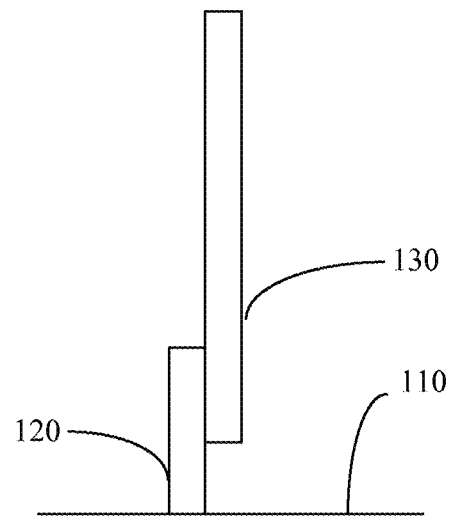
FIG. 1(A) illustrates a non-limiting example of capture of a target fragment with a capture oligonucleotide that is attached to a solid support.

Reference will now be made in detail to exemplary embodiments of the invention. While the invention will be described in conjunction with the exemplary embodiments, it will be understood that they are not intended to limit the invention to these embodiments. On the contrary, the invention is intended to encompass alternatives, modifications and equivalents, which may be included within the spirit and scope of the invention.

The invention relates to diverse fields impacted by the nature of molecular interaction, including chemistry, biology, medicine and diagnostics. The invention described herein has many embodiments and relies on many patents, applications and other references for details known to those of the art. Therefore, when a patent, application, or other reference is cited or repeated below, it should be understood that the entire disclosure of the document cited is incorporated by reference in its entirety for all purposes as well as for the proposition that is recited. All documents, e.g., publications and patent applications, cited in this disclosure, including the foregoing, are incorporated herein by reference in their entireties for all purposes to the same extent as if each of the individual documents were specifically and individually indicated to be so incorporated herein by reference in its entirety.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including, but not limited to, mammals, plants, bacteria, or cells derived from any of the above.

Throughout this disclosure, various aspects of this invention can be presented in a range format. It should be understood that when a description is provided in range format, this is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, for example, as well as individual numbers within that range, for example, 1, 2, 3, 4, 5, and 6. This applies regardless of the breadth of the range.

The practice of the invention described herein may employ, unless otherwise indicated, conventional techniques and descriptions of organic chemistry, polymer technology, molecular biology (including recombinant techniques), cell biology, biochemistry, and immunology, which are within the skill of one of skill in the art. Such conventional techniques include polymer array synthesis, hybridization, ligation, and detection of hybridization using a detectable label. Specific illustrations of suitable techniques are provided by reference to the examples hereinbelow. However, other equivalent conventional procedures may also be employed. Such conventional techniques and descriptions may be found in standard laboratory manuals, such as *Genome Analysis: A Laboratory Manual Series* (*Vols. I-IV*), *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995), *Biochemistry*, 4th Ed., Freeman, New York, Gait, *Oligonucleotide Synthesis: A Practical Approach*, (1984), IRL Press, London, Nelson and Cox (2000), Lehninger, *Principles of Biochemistry*, $3^{rd}$ Ed., W.H. Freeman Pub., New York, N.Y., and Berg et al. (2002), *Biochemistry*, $5^{th}$ Ed., W.H. Freeman Pub., New York, N.Y., all of which are herein incorporated in their entirety by reference for all purposes.

The invention may employ solid substrates, including arrays in some embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the described invention include, but are not limited to, those that are commercially available from Affymetrix (Santa Clara, Calif.) under the brand name GENECHIP®.

Many uses for polymers attached to solid substrates are contemplated herein. These uses include, but are not limited to, gene expression monitoring, profiling, library screening, genotyping and diagnostics. Methods of gene expression monitoring and profiling are described in U.S. Pat. Nos. 5,800,992, 6,013,449, 6,020,135, 6,033,860, 6,040,138, 6,177,248 and 6,309,822. Genotyping methods, and uses thereof, are disclosed in U.S. patent application Ser. No. 10/442,021 and U.S. Pat. Nos. 5,856,092, 6,300,063, 5,858, 659, 6,284,460, 6,361,947, 6,368,799, 6,333,179, and 6,872, 529. Other uses are described in U.S. Pat. Nos. 5,871,928, 5,902,723, 6,045,996, 5,541,061, and 6,197,506.

Also contemplated are sample preparation methods in certain embodiments. Prior to, or concurrent with, genotyping, the genomic sample may be amplified by a variety of mechanisms, some of which may employ PCR. (See, for example, *PCR Technology: Principles and Applications for DNA Amplification*, Ed. H. A. Erlich, Freeman Press, New York, N.Y., 1992; *PCR Protocols: A Guide to Methods and Applications*, Eds. Innis, et al., Academic Press, San Diego, Calif., 1990; Mattila et al., *Nucleic Acids Res.*, 19:4967, 1991; Eckert et al., *PCR Methods and Applications*, 1:17, 1991; *PCR*, Eds. McPherson et al., IRL Press, Oxford, 1991; and U.S. Pat. Nos. 4,683,202, 4,683,195, 4,800,159 4,965,188, and 5,333,675, each of which is incorporated herein by reference in their entireties for all purposes. The sample may also be amplified on the array. (See, for example, U.S. Pat. No. 6,300,070 and U.S. patent application Ser. No. 09/513,300, all of which are incorporated herein by reference).

Other suitable amplification methods include the ligase chain reaction (LCR) (see, for example, Wu and Wallace, *Genomics*, 4:560 (1989), Landegren et al., *Science*, 241:1077 (1988) and Barringer et al., *Gene*, 89:117 (1990)), transcription amplification (Kwoh et al., *Proc. Natl. Acad. Sci. USA*, 86:1173 (1989) and WO 88/10315), self-sustained sequence replication (Guatelli et al., *Proc. Nat. Acad. Sci. USA*, 87:1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid based sequence amplification (NABSA). (See also, U.S. Pat. Nos. 5,409,818, 5,554,517, and 6,063,603, each of which is incorporated herein by reference). Other amplification methods that may be used are described in, for instance, U.S. Pat. Nos. 6,582,938, 5,242,794, 5,494,810, and 4,988,617, each of which is incorporated herein by reference.

Additional methods of sample preparation and techniques for reducing the complexity of a nucleic sample are described in Dong et al., *Genome Research*, 11:1418 (2001), U.S. Pat. Nos. 6,361,947, 6,391,592, 6,632,611, 6,872,529 and 6,958,225, and in U.S. patent application Ser. No. 09/916,135.

Methods for conducting polynucleotide hybridization assays have been well developed in the art. Hybridization assay procedures and conditions will vary depending on the application and are selected in accordance with known general binding methods, including those referred to in Maniatis et al., *Molecular Cloning: A Laboratory Manual*, 2$^{nd}$ Ed., Cold Spring Harbor, N.Y, (1989); Berger and Kimmel, *Methods in Enzymology, Guide to Molecular Cloning Techniques*, Vol. 152, Academic Press, Inc., San Diego, Calif. (1987); Young and Davism, *Proc. Nat'l. Acad. Sci.*, 80:1194 (1983). Methods and apparatus for performing repeated and controlled hybridization reactions have been described in, for example, U.S. Pat. Nos. 5,871,928, 5,874,219, 6,045,996, 6,386,749, and 6,391,623 each of which are incorporated herein by reference.

The invention also provides signal detection of hybridization between ligands in certain embodiments. (See, U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625, U.S. patent application Ser. No. 10/389,194 (U.S. Patent Application Publication No. 2004/0012676, allowed) and PCT Application PCT/US99/06097 (published as WO 99/47964), each of which is hereby incorporated by reference in its entirety for all purposes).

The practice of the inventions herein may also employ conventional biology methods, software and systems. Computer software products of the invention typically include, for instance, computer readable medium having computer-executable instructions for performing the logic steps of the method of the invention. Suitable computer readable medium include, but are not limited to, a floppy disk, CD-ROM/DVD/DVD-ROM, hard-disk drive, flash memory, ROM/RAM, magnetic tapes, and others that may be developed. The computer executable instructions may be written in a suitable computer language or combination of several computer languages. Basic computational biology methods which may be employed in the invention are described in, for example, Setubal and Meidanis et al., *Introduction to Computational Biology Methods*, PWS Publishing Company, Boston, (1997); Salzberg, Searles, Kasif, (Ed.), *Computational Methods in Molecular Biology*, Elsevier, Amsterdam, (1998); Rashidi and Buehler, *Bioinformatics Basics: Application in Biological Science and Medicine*, CRC Press, London, (2000); and Andreas D. Baxevanis and B. F. Francis Ouellette, *Bioinformatics: A Practical Guide to the Analysis of Gene and Proteins*, Wiley-Interscience, 2$^{nd}$ ed., (2001); and also U.S. Pat. No. 6,420,108.

The invention may also make use of various computer program products and software for a variety of purposes, such as probe design, management of data, analysis, and instrument operation. (See, e.g., U.S. Pat. Nos. 5,593,839, 5,795,716, 5,733,729, 5,974,164, 6,066,454, 6,090,555, 6,185,561, 6,188,783, 6,223,127, 6,229,911 and 6,308,170).

Additionally, the invention encompasses embodiments that may include methods for providing genetic information over networks such as the internet, as disclosed in, for instance, U.S. patent application Ser. No. 10/197,621 (U.S. Patent Application Publication No. 20030097222), Ser. No. 10/063,559 (U.S. Patent Application Publication No. 20020183936, , Ser. No. 10/065,856 (U.S. Patent Application Publication No. 20030100995, , Ser. No. 10/065,868 (U.S. Patent Application Publication No. 20030120432, , Ser. No. 10/328,818 (U.S. Patent Application Publication No. 20040002818, , Ser. No. 10/328,872 (U.S. Patent Application Publication No. 20040126840, , Ser. No. 10/423,403 (U.S. Patent Application Publication No. 20040049354, and 60/482,389.

II. Definitions of Selected Terms

The term "array" as used herein refers to an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). The molecules in the array can be identical or different from each other. Additionally, the term "array" is meant to include those libraries of "nucleic acids" which can be prepared by spotting nucleic acids of essentially any length (e.g., from 1 to about 1000 nucleotide monomers in length) onto a substrate.

The term "binding protein" as used herein refers to a protein which has either a specific or general binding affinity for nucleic acids. The nucleic acids may be either DNA or RNA, and additionally may be either single-stranded or double-stranded. These binding proteins may interact through any possible mechanism, with non-limiting examples being interaction through the major groove or the minor groove. Binding proteins include at least one binding domain, a portion of the protein that recognizes single-stranded or double-stranded DNA or RNA, either specifically or non-specifically. If a binding protein has specific binding properties, then the binding protein will preferentially bind to one or more "recognition sites," defined separately herein, depending upon the corresponding "recognition sequence" or "recognition sequences," also defined separately herein, for which the binding domain of a binding protein will recognize for further interaction and binding. Binding proteins may also be associated with one or more accessory molecules, such as cofactor proteins, which may affect the binding affinity which a particular binding protein possesses for a recognition site. Binding proteins may additionally be associated with one or more steps to activate or otherwise modify the binding protein before certain steps within the assay. Non-limiting examples of such activation or modification steps include phosphorylation, acetylation and methylation.

The term "capture oligonucleotide" as used herein refers to an "oligonucleotide," defined separately herein, utilized in capturing a target fragment. Capture oligonucleotides may be any form of "nucleic acid" as defined herein. The length of capture oligonucleotide will vary depending upon the particular embodiment, the length of the target fragment, the length of the "recognition sequence" of the "recognition site." Non-limiting examples of the length for capture oligonucleotides include between 10 and 100 nucleotides, for example, 10, 11, 12, 13, 14, 15, 16, 17, 18, 19, 20, 25, 30, 35, 40, 45, 50, 60, 75 or 90 nucleotides. Other lengths within this range, as well as shorter and longer lengths (e.g., 8, 9, 105, 110) are also possible depending upon the embodiment. One or more capture oligonucleotides may be utilized with respect to a single recognition site (e.g., a first and second capture oligonucleotide). Many embodiments include one or more capture oligonucleotides attached to one or more substrates, wherein attachment includes, for instance, attaching pre-synthesized capture oligonucleotides to the substrate or in situ synthesis of the capture oligonucleotides. Depending upon the embodiment, a single substrate may have one or more copies of one or more particular capture oligonucleotides. Other embodiments, however, do not attach capture oligonucleotides to substrates.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "complementary fragment" as used herein refers to a complementary nucleic acid strand that is synthesized in order to make the "target fragment," defined separately herein, double-stranded. The complementary fragment may be made through any viable method. A non-limiting example is enzymatically through the use of a DNA polymerase. The length and identity of the nucleotides at each position of the complementary fragment depend upon the length and sequence identity of the target fragment. Furthermore, a complementary fragment is not required for all embodiments, as binding proteins which are specific for single-stranded recognition sites may not bind if the recognition site has been made double-stranded through the synthesis of a complementary fragment. However, a complementary fragment may still be utilized in embodiments directed at single-stranded binding proteins. A non-limiting example of such a use would be the creation of a single-stranded recognition site through extension of the capture oligonucleotide, subsequent separation of the strands, and removal of the single-stranded target fragment to free the recognition site on the strand containing the capture oligonucleotide and the complementary fragment for possible binding.

The term "complementary region" or "complementary portion" as used herein refers to one or more regions of nucleotides of one or more capture oligonucleotides that are complementary to a target fragment. The number of complementary regions generally, but not necessarily, equals the number of capture oligonucleotides associated with a particular recognition site (e.g., if two capture oligonucleotides are utilized to capture a particular target fragment, there will generally be at least two complementary regions). The complementary region may be, but is not required to be, a unique sequence with respect to the genome of the sample at issue or the processed sample (which may have a lower complexity than the overall genome due to complexity reduction, selective amplification, etc.). The complementary region may also be a unique, conserved sequence. The length of the complementary region will depend upon the embodiment and factors such as the desired specificity. The complementary region may be, for example, from 10 to 100 nucleotides in length (e.g., 10, 11, 12, 13, 14, 15, 16, 17, 18, 19, 20, 25, 30, 35, 40, 45, 50, 60, 75 or 90 nucleotides). Other lengths within this range, as well as shorter and longer lengths (e.g., 8, 9, 105, 110) are also possible depending upon the embodiment.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis, "Molecular Cloning A laboratory Manual" $2^{nd}$ Ed. Cold Spring Harbor Press (1989), which is hereby incorporated by reference in its entirety for all purposes above. Hybridizations, e.g., allele-specific probe hybridizations, are generally performed under stringent conditions. For example, conditions where the salt concentration is no more than about 1 Molar (M) and a temperature of at least 25° C., e.g., 750 mM NaCl, 50 mM Sodium Phosphate, 5 mM EDTA, pH 7.4 (5×SSPE) and a temperature of from about 25 to about 30° C.

The term "hybridizing specifically to" as used herein refers to the binding, duplexing, or hybridizing of a molecule only to a particular nucleotide sequence or sequences under stringent conditions when that sequence is present in.

The term "label" as used herein refers to a molecule or combination of molecules which facilitate detection of a binding protein or a nucleic acid. The label may be a detectable chemical or biochemical moiety or a signal obtained from an enzyme-linked assay. The label molecule(s) can be applied directly to the label target or indirectly through the use of two or more sets of molecules, antibodies, etc. Non-limiting examples of fluorescent labels include organic dyes, biological fluorophores, and quantum dots. Labels may include the use of antibodies. Non-limiting examples of antibody labeling techniques include radioisotopes, enzymatic tags, and fluorescent tags.

The term "mutation" or "polymorphism" as used herein refers to the occurrence of two or more genetically determined alternative sequences or alleles in a population. A polymorphic marker or site is the locus at which divergence occurs. A mutation may comprise one or more base changes, an insertion, a repeat, or a deletion. Larger mutations may comprise one or more amplifications or duplications, deletions, translocations, interstitial deletions, inversions, or a loss of heterozygosity with respect to chromosomal structural. A polymorphic locus may be as small as one base pair. Polymorphic markers include restriction fragment length polymorphisms, variable number of tandem repeats, hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild-type form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "nucleic acid" or "nucleic acids" as used herein refers to a polymeric form of nucleotides of any length, for example ribonucleotides, deoxyribonucleotides, locked nucleic acids (LNAs) or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated, hydroxymethylated or glucosylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "oligonucleotide" or "polynucleotide," as used interchangeably herein, refers to a nucleic acid ranging from at least 2, preferably at least 8, and more preferably at least 15 nucleotides in length or a compound that specifically hybridizes to a polynucleotide. Polynucleotides of the invention include sequences of deoxyribonucleic acid (DNA) or ribonucleic acid (RNA) which may be isolated from natural sources, recombinantly produced or artificially synthesized and mimetics thereof. A further example of a polynucleotide of the invention may be locked nucleic acids (LNAs) or peptide nucleic acid (PNA). The invention also encompasses situations in which there is a nontraditional base pairing such as Hoogsteen base pairing which has been identified in certain tRNA molecules and postulated to exist in a triple helix.

The term "primer" as used herein refers to a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site or primer binding site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "recognition sequence" as used herein refers to the sequence of DNA or RNA for which the binding domain of a binding protein may exhibit binding specificity. A recognition sequence is the sequence or sequences of nucleotides recognized by the binding domain of the particular protein, with the number and identity of the nucleotides within the sequence dependent upon the binding protein at issue. Thus, some recognition sequences will be shorter (e.g., 6 nucleotides) in length than others (e.g., 15 nucleotides), but it should be appreciated that the length and identity of any recognition sequence depends upon the one or more binding domains of the binding protein at issue. While some proteins may exhibit binding that is specific to only one particular recognition sequence, other binding proteins may bind to a plurality of recognition sequences. The plurality of recognition sequences may differ in any number of ways, such as smaller changes consisting of a single base change (e.g., a binding protein associated with two recognition sequences that contain either a guanine or thymine at a particular position), or larger changes (e.g., a change in the number of nucleotides in the sequence and a change in the identity of two or more bases).

The term "recognition site" as used herein refers to the location within the DNA or RNA sequence(s) where a recognition sequence is located. Depending upon the length of the sequence(s) at issue, and the length and identity of the recognition sequence, a particular recognition sequence may occur at more than one recognition site. Furthermore, if a binding protein is capable of binding to a plurality of recognition sequences (e.g., a binding protein which will bind to any of three recognition sequences which differ in length and/or identity of bases), there may be one or more recognition sites for that binding protein within a particular sequence(s) of DNA or RNA.

The term "sample" as used refers to any collection of nucleic acids. A sample may contain only desired nucleic acids, such as desired target fragments, or may additionally contain undesired nucleic acids as well as non-nucleic acid molecules. Non-limiting examples of samples include total genomic DNA, total RNA or total mRNA. Additionally, samples may have their complexity reduced, such as by fragmentation followed by adaptor ligation and amplification of the fragments. Moreover, a sample of nucleic acids may have been enriched for a given population but may still include other undesirable populations. For example, a sample of nucleic acids may be enriched for a desired set of DNA sequences but may still include some undesired DNA sequences. A sample may be from any particular organism, eukaryotic or prokaryotic. Non-limiting examples of organisms include humans, chimpanzees, dogs, rats, *Saccharomyces cerevisiae*, and *Escherichia coli*. Furthermore, a sample may be from an individual organism, a collection of organisms, or recombinantly or artificially produced.

The term "single-nucleotide polymorphism" ("SNP") as used herein refers to a DNA sequence variation occurring when a single nucleotide—A, T, C, or G—in the genome (or other shared sequence) differs between members of a species (or between paired chromosomes in an individual). For example, two sequenced DNA fragments from different individuals, AAGC$\underline{C}$TA to AAGC$\underline{T}$TA, contain a difference in a single nucleotide. In this case we say that there are two alleles: C and T.

The term "substrate" as used herein refers to a material or group of materials having a rigid or semi-rigid surface or surfaces. In some embodiments, at least one surface of the solid support will be substantially flat, although in some embodiments it may be desirable to physically separate synthesis regions for different compounds with, for example, wells, raised regions, pins, etched trenches, or the like. According to various embodiments, the solid support(s) will also take the form of, for example, wafers, chips, beads, resins, gels, microspheres, microparticles, slides, or other geometric configurations. Any suitable material(s) may be used for the substrate, including biological, non-biological, organic, and inorganic materials, or any combination of these. Non-limiting examples of materials for substrates include but are not limited to Si, Ge, GeAs, GaP, $SiO_2$, $SiN_4$, other silicon based materials, glass, fused silica, fused quartz, polyvinylidene fluoride, polycarbonate, other polymers, combinations of these, and other suitable materials known in the art The term "target fragment" or "target nucleic acid sequence" or "target sequence" as used interchangeably herein refers to a nucleic acid sequence which contains one or more regions or portions that are complementary to at least one capture oligonucleotide. Non-limiting examples include a nucleic acid containing a single region which is complementary to a specific capture oligonucleotide, and a nucleic acid which contains two complementary regions, each of which is complementary to a different capture oligonucleotide. The length of the target fragment may be any suitable size, but preferably includes, in addition to the one or more complementary portions, the entirety of a recognition site, such that all of the nucleotides of that recognition site's recognition sequence are included within the target fragment, or within the complement of the target fragment. A sample, however, may contain undesired target fragments which do not contain the desired recognition site, or only contain a portion of the desired recognition site's recognition sequence.

III. Biological Microarrays

A biological microarray often includes nucleic acid oligonucleotide probes that are used to extract information related to, for example, various nucleic acid samples, and other related substances of interest, such as nucleic acid binding proteins. The nucleic acid samples are exposed to the nucleic acid probes under certain conditions that allow hybridization. The sample nucleic acids may be labeled with a detectable chemical moiety, such as a fluorescent dye, or signal obtained from an enzyme-linked assay. Additional steps may also be performed before processing and scanning, depending upon the particular application of the microarray and the desired information.

A variety of techniques are known for the creation and use of arrays of different biological polymers, such as nucleic acid and polypeptide arrays. Many techniques have been commercialized, such as Affymetrix® arrays (Affymetrix, Inc., Santa Clara, Calif.) in the form of GeneChip® array cartridges, array strips, and Axiom® array plates. Other commercialized arrays include Agilent® arrays (Agilent Technologies, Inc., Santa Clara, Calif.), Illumina® arrays (Illumina, Inc., San Diego, Calif.) and NimbleGen® arrays (Roche NimbleGen, Inc., Madison, Wis.). Such arrays may contain hundreds, thousands, or millions of different polynucleotide or polypeptide sequences, depending upon the abilities of the particular manufacturing technique at issue with respect to feature size, the size of the relevant solid support of silicon, glass, or other material, the desired characteristics of the relevant assay, and other factors.

A variety of techniques are known for the creation and use of arrays of different biological polymers, such as nucleic acid and polypeptide arrays. See, e.g., U.S. Pat. No. 5,143, 854 to Pirrung et al.; U.S. Pat. No. 5,744,305 to Fodor et al.; U.S. Pat. No. 7,332,273 to Trulson et al.; U.S. Pat. Nos. 5,945,334 and 6,140,044 to Besemer et al.; U.S. Pat. No. 5,545,531 to Rava et al.; U.S. Pat. No. 6,660,233 to Coassin et al.; U.S. Patent Application Publication Nos. 2004/ 0038388 and 2006/0088863 to Yamamoto et al.; U.S. Patent Application Publication No. 2005/0023672 to Oostman et al.; U.S. Patent Application Publication No. 2008/0003667 to Jones et al.; U.S. Patent Application Publication Nos. 2006/0246576, 2006/0234371, 2011/0136699 and 2010/

0248981 to Shirazi; pending U.S. patent application Ser. No. 13/157,268, filed Jun. 9, 2011; U.S. Pat. No. 6,242,266 to Schleifer et al.; U.S. Pat. No. 6,375,903 to Cerrina et al.; U.S. Pat. No. 5,436,327 to Southern et al.; U.S. Pat. No. 5,474,796 to Brennan; U.S. Pat. No. 5,658,802 to Hayes et al.; U.S. Pat. No. 5,770,151 to Roach et al.; U.S. Pat. No. 5,807,522 to Brown et al.; U.S. Pat. No. 5,981,733 to Gamble et al.; U.S. Pat. No. 6,101,946 to Martinsky; U.S. Pat. Nos. 6,355,431 and 6,429,027 to Chee et al.; U.S. Pat. No. 7,510,841 to Stuelpnagel et al., U.S. Pat. Nos. 7,745,091 and 7,745,092 to True; U.S. Patent Application Publication No. 2010/0297448 to True et al.; and U.S. Patent Application Publication Nos. 2010/0227279, 2010/0227770 and 2009/0149340 to True, all of which are expressly incorporated herein by reference for all purposes.

A non-limiting example of arrays which are suitable for use with certain embodiments include Affymetrix GENECHIP® arrays, which are synthesized in accordance with techniques sometimes referred to as VLSPS™ (Very Large Scale Immobilized Polymer Synthesis) technologies. Some aspects of VLSPS™ and other microarray manufacturing technologies are described in U.S. Pat. Nos. 5,424,186; 5,143,854; 5,445,934; 5,744,305; 5,831,070; 5,837,832; 6,022,963; 6,083,697; 6,291,183; 6,309,831; and 6,310,189, all of which are hereby incorporated by reference in their entireties for all purposes. The probes of these arrays in some implementations consist of nucleic acids that are synthesized by methods including the steps of activating regions of a substrate and then contacting the substrate with a selected monomer solution. As used herein, nucleic acids may include any polymer or oligomer of nucleosides or nucleotides (polynucleotides or oligonucleotides) that include pyrimidine and/or purine bases, preferably cytosine, thymine, and uracil, and adenine and guanine, respectively. Nucleic acids may include any deoxyribonucleotide, ribonucleotide, and/or peptide nucleic acid component, and/or any chemical variants thereof such as LNAs, methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Probes of other biological materials, such as peptides or polysaccharides as non-limiting examples, may also be formed. For more details regarding possible implementations, see U.S. Pat. No. 6,156,501, which is hereby incorporated by reference herein in its entirety for all purposes.

A system and method for efficiently synthesizing probe arrays using masks is described in U.S. Pat. No. 6,949,638, which is hereby incorporated by reference herein in its entirety for all purposes. A system and method for a rapid and flexible microarray manufacturing and online ordering system is described in U.S. Provisional Patent Application Ser. No. 60/265,103 (now expired), filed Jan. 29, 2001, which also is hereby incorporated herein by reference in its entirety for all purposes. Systems and methods for optical photolithography without masks are described in U.S. Pat. No. 6,271,957 and in U.S. patent application Ser. No. 09/683,374 filed Dec. 19, 2001, both of which are hereby incorporated by reference herein in their entireties for all purposes.

The probes of synthesized probe arrays typically are used in conjunction with biological target molecules of interest, such as cells, proteins, genes or EST's, other DNA sequences, or other biological elements. More specifically, the biological molecule of interest may be a ligand, receptor, peptide, nucleic acid (oligonucleotide or polynucleotide of RNA or DNA), or any other of the biological molecules listed in U.S. Pat. No. 5,445,934 (incorporated by reference above) at column 5, line 66 to column 7, line 51. For example, if transcripts of genes are the interest of an experiment, the target molecules would be the transcripts. Other examples include protein fragments and small molecules. Target nucleic acid refers to a nucleic acid (often derived from a biological sample) of interest. Frequently, a target molecule is detected using one or more probes. As used herein, a probe is a molecule for detecting a target molecule. A probe may be any of the molecules in the same classes as the target referred to above. As non-limiting examples, a probe may refer to a nucleic acid, such as an oligonucleotide, capable of binding to a target nucleic acid of complementary sequence through one or more types of chemical bonds, usually through complementary base pairing, usually through hydrogen bond formation. As noted above, a probe may include natural, e.g. A, G, U, C, or T, or modified bases (7-deazaguanosine, inosine, LNA, PNA, for example). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that these are illustrative embodiments that are not to limit the invention in any way.

The samples or target molecules of interest (hereafter, simply targets) are processed so that, typically, they are spatially associated with certain probes in the probe array. For example, one or more tagged targets are distributed over the probe array. In accordance with some implementations, some targets hybridize with probes and remain at the probe locations, while non-hybridized targets are washed away. These hybridized targets, with their tags or labels, are thus spatially associated with the probes. The hybridized probe and target may sometimes be referred to as a probe-target pair. Detection of these pairs can serve a variety of purposes, such as to determine whether a target nucleic acid has a nucleotide sequence identical to or different from a specific reference sequence. (See, for example, U.S. Pat. No. 5,837,832, referred to and incorporated above). Other uses include gene expression monitoring and evaluation (see, e.g., U.S. Pat. No. 5,800,992, U.S. Pat. No. 6,040,138, and International Patent App. No. PCT/US98/15151, published as WO99/05323), genotyping (U.S. Pat. No. 5,856,092), or other detection of nucleic acids. The '992, '138, and '092 patents, and publication WO99/05323, are incorporated by reference herein in their entireties for all purposes.

Other techniques exist for depositing probes on a substrate or support. For example, "spotted arrays" are commercially fabricated, typically on microscope slides. These arrays consist of liquid spots containing biological material of potentially varying compositions and concentrations. For instance, a spot in the array may include a few strands of short oligonucleotides in a water solution, or it may include a high concentration of long strands of complex proteins. There are devices that deposit densely packed arrays of biological materials on microscope slides in accordance with these techniques. Aspects of these and other spot arrayers are described in U.S. Pat. Nos. 6,040,193 and 6,136,269, in U.S.

Pat. No. 6,955,788, and in International Patent Application No. PCT/US99/00730 (International Publication Number WO 99/36760), all of which are hereby incorporated by reference in their entireties for all purposes. Other techniques for generating spotted arrays also exist. For example, U.S. Pat. No. 6,040,193 to Winkler, et al., is directed to processes for dispensing drops to generate spotted arrays. The '193 patent, and U.S. Pat. No. 5,885,837 to Winkler, also describe the use of micro-channels or micro-grooves on a substrate, or on a block placed on a substrate, to synthesize arrays of biological materials. These patents further describe separating reactive regions of a substrate from each other by inert regions and spotting on the reactive regions. The '193 and '837 patents are hereby incorporated by reference in their entireties. Another technique is based on ejecting jets of biological material to form a spotted array. Other implementations of the jetting technique may use devices such as syringes or piezo electric pumps to propel the biological material. Various other techniques exist for synthesizing, depositing, or positioning biological material onto or within a substrate.

To ensure proper interpretation of the term "probe" as used herein, it is noted that contradictory conventions exist in the relevant literature. The word "probe" is used in some contexts to refer not to the biological material that is synthesized on a substrate or deposited on a slide, as described above, but to what has been referred to herein as the "target." To avoid confusion, the term "probe" is used herein to refer to probes such as those synthesized according to the VLSPS™ technology and other synthesis techniques known in the art; the biological materials deposited so as to create spotted arrays; and materials synthesized, deposited, or positioned on a substrate to form arrays according to other current or future technologies. Thus, microarrays formed in accordance with any of these technologies may be referred to generally and collectively hereafter for convenience as "probe arrays." Moreover, the term "probe" is not limited to probes immobilized in array format. Rather, the functions and methods described herein may also be employed with respect to other parallel assay devices. For example, these functions and methods may be applied with respect to probe-set identifiers that identify probes immobilized on or in beads, optical fibers, or other substrates or media.

Probes typically are able to detect the expression of corresponding genes or EST's by detecting the presence or abundance of mRNA transcripts present in the target. This detection may, in turn, be accomplished by detecting labeled cRNA that is derived from cDNA derived from the mRNA in the target. In general, a group of probes, sometimes referred to as a probe set, contains sub-sequences in unique regions of the transcripts and does not correspond to a full gene sequence. Further details regarding the design and use of probes are provided in U.S. Pat. No. 6,188,783, in International Patent Application Ser. No. PCT/US01/02316, filed Jan. 24, 2001, and in U.S. patent application Ser. No. 09/721,042, Ser. No. 09/718,295, and Ser. No. 09/764,324, and U.S. Pat. No. 7,117,095, all of which patents and patent applications are hereby incorporated herein by reference in their entireties for all purposes.

Labeled targets in hybridized probe arrays may be detected using various commercial devices, sometimes referred to as scanners. Scanners image the targets by detecting fluorescent or other emissions from the labels, or by detecting transmitted, reflected, or scattered radiation. A typical scheme employs optical and other elements to provide excitation light and to selectively collect the emissions. Also generally included are various light-detector systems employing photodiodes, charge-coupled devices, photomultiplier tubes, or similar devices to register the collected emissions. For example, a scanning system for use with a fluorescent label is described in U.S. Pat. No. 5,143,854, incorporated by reference above. Other scanners or scanning systems are described in U.S. Pat. Nos. 5,578,832, 5,631,734, 5,834,758, 5,936,324, 5,981,956, 6,025,601, 6,141,096, 6,185,030, 6,490,533, 6,650,411, 6,643,015 and 6,201,639, in International Patent Application PCT/US99/06097 (published as WO99/47964), in U.S. patent application Ser. No. 09/682,837, and in U.S. Provisional Patent Application Ser. Nos. 60/364,731, 60/396,457, and 60/435,178, each of which patent and patent application is hereby incorporated by reference in its entirety for all purposes.

It is further contemplated that assays of the present invention will utilize, in some embodiments, "liquid arrays." As used herein, a liquid array typically consists of a plurality of encoded microparticles where each microparticle has been encoded with one or more features comprising a distinguishable, pre-determined code. One or more probes can be immobilized on the surface of each microparticle, often with probes immobilized on a single particle at densities of, for example, $10^4/um^2$ or higher. Incorporation of distinguishable, pre-determined codes allows for each desired species of probe to be immobilized upon microparticles of a single distinct code. Assays will then typically hybridize the probes immobilized on a microparticle with one or more targets from one or more samples. Labeling methods known in the art can be used with respect to the samples, microparticles, or both depending on the design of a particular assay. Subsequent detection and quantification of the various targets is performed by detection and reading of the codes on the microparticles and detection and quantification of the desired label to provide both detection and quantification of the targets. Further details regarding the design and use of liquid arrays are provided in U.S. Pat. Nos. 7,745,091; 7,745,092; U.S. Published Patent Application Nos. 2009/0149340; 2010/0227770; 2010/0227279; 2010/0290018; 2010/0297336; 2010/0297448; and U.S. Patent Application Ser. Nos. 60/716,694; 60/762,238; 60/946,127; and Ser. No. 11/521,115, each of which are hereby incorporated herein by reference in their entireties for all purposes.

IV. Specific Embodiments

Various embodiments are contemplated herein relating to assays that capture recognition sites for DNA or RNA binding proteins, convert the recognition sites into double-stranded form if necessary, bind DNA or RNA binding proteins to the recognition sites, and measure the resulting binding affinities of the selected binding proteins for the particular recognition sequences of the recognition sites.

Figure 1B:
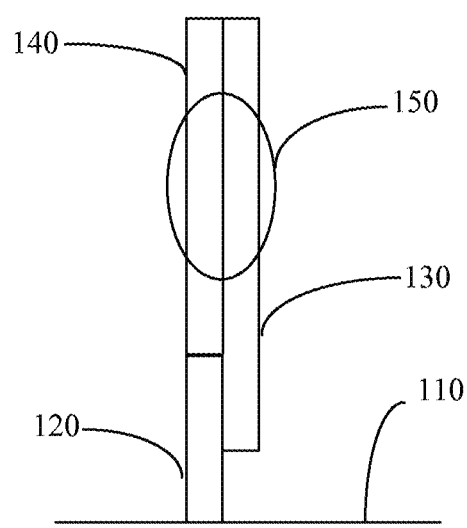
FIG. 1(B) illustrates a non-limiting example of extension of the capture oligonucleotide based upon the target fragment captured in FIG. 1(A), thus forming a double-stranded protein binding site.
Figure 1C:
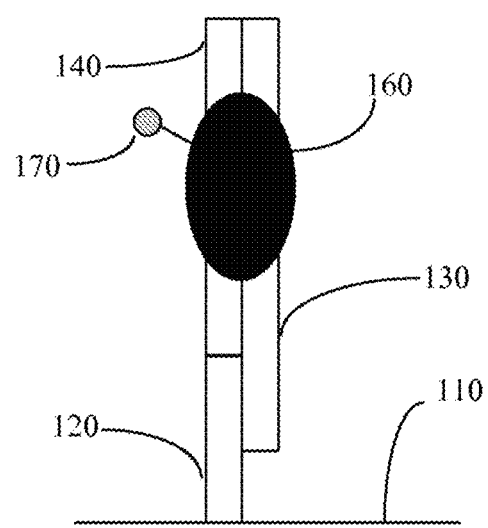
FIG. 1(C) illustrates a non-limiting example of binding of a labeled binding protein to the double-stranded protein binding site formed in FIG. 1(B).

Aspects of certain embodiments of the assay are illustrated by FIG. 1(A)-1(C). In FIG. 1(A), a capture oligonucleotide 120 is attached to a substrate 110. Capture oligonucleotide 120 may be a sequence of DNA or RNA, isolated from natural sources, recombinantly produced or artificially synthesized, and can include modified artificial analogs thereof, such as locked nucleic acids or peptide nucleic acids. The sequence length of capture oligonucleotide 120 will vary depending on the particular embodiment, but will generally be at least 10 nucleotides in length, and may be significantly longer in length, such as lengths of 100 nucleotides. Sequence lengths within these two values are also possible, for example, lengths of 10, 11, 12, 13, 14, 15, 20, 25, 30, 35, 40, 50, 60, 75, or 90 nucleotides. Other embodiments may utilize sequence lengths for capture oligonucleotide outside of this range, such as 8, 9, 105 or 110 nucleotides. Capture oligonucleotide 120 may be attached to substrate 110 at its 5' or 3' end. It should be further noted that substrate 110 can be any suitable substrate as discussed herein, and configured for a variety of array formats, including, for example, Affymetrix GENECHIP® arrays, other high density microarray formats, spotted arrays, liquid arrays, inkjet arrays, bead arrays and other array formats compatible with the various embodiments disclosed herein. Capture oligonucleotide 120 may be attached to substrate 110 through in situ synthesis via, for example, a photolithographic approach utilizing photodeprotection with masks, photolithography utilizing digital micromirrors, or an inkjet printing approach utilizing chemical deprotection. Capture oligonucleotide 120 may also be attached to substrate 110 after capture oligonucleotide 120 has been synthesized, such as by covalent attachment via an aliphatic amine group at the 5' end of capture oligonucleotide 120. Additionally, capture oligonucleotide 120 may be directly attached to substrate 110, or through other means known in the art, such as through a linker molecule, for example lysine, epoxy-silanes (e.g., 3-glycidoxypropyl trimethoxysilane), or amino-silanes (e.g., 3-aminopropyl trimethoyxsilane), or many other alternatives known in the art. Furthermore, each substrate 110 may have a single capture oligonucleotide 120, multiple copies of a particular capture oligonucleotide 120, single copies of a plurality of different capture oligonucleotides 120, or multiple copies of a plurality of different capture oligonucleotides 120. Capture oligonucleotides 120 may be attached in any suitable arrangement and density, such as in a pre-determined grid, a random attachment with subsequent identification of the location of each capture oligonucleotide 120, or through other means known in the art. Substrate 110 may include additional components depending upon the embodiment. For example, embodiments utilizing liquid arrays comprise a plurality of microparticles, where each microparticle has been encoded with one or more features comprising a distinguishable, pre-determined code. Subsequent detection of the code, in correlation with the capture oligonucleotides 120 attached to the microparticle substrate, facilitates the measurement of binding affinities of various binding proteins for one or more recognition sites. Other embodiments, for example, may attach one or more capture oligonucleotide 120s to other substrates, such as beads, where the substrate is individually distinguishable from other substrates within the assay that possess different capture oligonucleotides. Such beads have been commercialized within, for instance, the xMAP® technology for multiplexing utilizing color-coded microspheres (Luminex Corporation, Austin, Tex.). It should be noted, however, that not all embodiments will attach capture oligonucleotides 120 to a substrate. Alternative embodiments may maintain capture oligonucleotides 120, for example, in-solution.

Capture oligonucleotide 120 includes a complementary region (or complementary portion, as used interchangeably herein) that is complementary to at least a portion of target fragment 130, and which will hybridize with target fragment 130, as illustrated in FIG. 1(A). Furthermore, in certain embodiments, the complementary portion of capture oligonucleotide 120 is a unique sequence. The uniqueness may be with respect to, for example, the overall genome of the sample at issue, or merely the prepared and processed sample (e.g., after selective amplification or other complexity reduction methods). The complementary portion is also a unique, conserved sequence in some embodiments. The distance between the complementary portion of capture oligonucleotide 120 and recognition site 150 will vary depending upon the embodiment. In some embodiments there will be no intervening nucleotides between the complementary portion of capture oligonucleotide 120 and the first nucleotide of the recognition sequence of recognition site 150. In other embodiments, there may be a number of intervening nucleotides, for example, between 1 and 100 nucleotides, such as 1, 5, 10, 15, 20, 30, 40, 50, 75, 100, 150, 200 or more nucleotides. The number of intervening nucleotides may also fall within this range. Embodiments which may utilize a number of intervening nucleotides include, for example, embodiments where it is desired for the complementary portion of capture oligonucleotide 120 to be a unique sequence, or a unique conserved sequence, which depending on the distance to the nearby recognition site of interest, may require a number of intervening nucleotides.

In some embodiments, the complementary portion of capture oligonucleotide 120 may consist of the entirety of capture oligonucleotide 120, while in other embodiments only a segment of capture oligonucleotide 120 is complementary to target fragment 130. FIG. 1(A)-1(C) depict embodiments where there is at least one nucleotide of capture oligonucleotide 120 that is not complementary to target nucleic acid fragment 130. Furthermore, the length of the complementary portion will vary depending on the embodiment and desired characteristics of the array. For example, if higher specificity with respect to target nucleic acid fragment 130 is desired, the complementary portion may be, for example, 25, 30, 35, 40, 45, 50, 60 or 70 nucleotides in length (as well as nucleotide lengths within this range and longer nucleotide lengths). If the desired array is to contain a larger number of capture oligonucleotides 120 for a lower relative cost, then the complementary portion may be smaller in length, for example 8, 9, 10, 11, 12, 13, 14, 15, 16, 17, 18, 19, 20, 21, 22, 23, 24, or 25. Additionally, the length of the complementary portion, and the length of capture oligonucleotide 120 in general, will depend on other factors, such as the desired method of producing capture oligonucleotide 120. The length of the complementary portion will directly affect the required length of capture oligonucleotide 120. For instance, if a complementary portion length of 25 nucleotides is desired, then capture oligonucleotide 120 must be at least 25 nucleotides in length. In some embodiments, capture oligonucleotide 120 includes additional portions. These additional portions may provide supplemental functionality, such as a specific address portion to enable precise identification of capture oligonucleotide 120. Thus, in some embodiments, in addition to the complementary portion, capture oligonucleotide 120 may include a unique sequence of nucleotides to aid in the exact identification of capture oligonucleotide 120 relative to other capture oligonucleotides 120 that may be utilized within the same assay or upon the same substrate. In such embodiments, the minimum length of capture oligonucleotide 120 will be dependent upon, for example, both the length of the complementary portion and also the length of the identification sequence. For example, if length of the complementary portion is 50 nucleotides and the length of the identification portion is 29 nucleotides, then capture oligonucleotide 120 will be at least 79 nucleotides in length.

Target fragment 130 is a nucleic acid sequence. Target fragment 130 may be from any sample of interest, taken from any particular organism of interest, eukaryotic or prokaryotic. Non-limiting examples include, e.g., human, chimpanzee, dog, rat, *Saccharomyces cerevisiae*, or *Escherichia coli* samples. In other embodiments, target fragment 130 is not from a sample taken from an organism, but is the result of recombinant synthesis, artificial synthesis, etc. For example, mutations within a recognition sequence can significantly affect the binding affinity of a binding protein for that recognition sequence, and some embodiments may utilize one or more synthesized mutant target fragments 130 with one or more mutations, such as SNPs, insertions, deletions or inversions, within the recognition sequence of recognition site 150. Accordingly, certain embodiments may use a plurality of differing target fragments 130 within a single assay, with the number depending upon factors such as the type and number of substrate employed, desired array characteristics, and the number of binding proteins and recognition sites of interest. Thus, embodiments may include libraries of various target fragments 130 with a plurality of mutations introduced such that a plurality of recognition site 150 variants are assayed for their binding affinity with the binding proteins of interest.

Target fragment 130 may be processed and prepared for the assay through any suitable means known in the art. For example, a sample may be taken from an individual organism, and then amplified by polymerase chain reaction, ligase chain reaction, transcription-based amplification, modifications thereof, and other techniques. For instance, a genomic DNA sample may be digested with restriction enzymes, such as Nsp I and Sty I, before adaptor ligation to the resulting fragments, PCR amplification of the adaptor-ligated fragments, and subsequent fragmentation (e.g., through restriction enzymes or acoustical shearing) of the amplified DNA. In some embodiments, target fragment 130 may be introduced to substrate 110 with an adaptor sequence added to one or both ends. Various techniques known in the art can be utilized to improve the quality of target fragments 130. For example, amplification of the target sample is useful in minimizing the influence of methylated DNA, where methylation may partially obstruct binding proteins from successfully binding to a recognition site. Methylation may also cause the target fragment 130 to already be bound by other binding proteins, such as methyl-CpG-binding domain proteins, which bind to methylated gene promoters. However, it should be noted that in some embodiments, maintaining the methylation that may be present in the original sample may be desirable. In such circumstances, various techniques may be used to prevent demethylation, such as the inclusion of DNA methyltransferase 1, during amplification of the sample.

FIG. 1(B) illustrates the next step in certain embodiments of the assay. Here, at least a portion of target fragment 130 that remains single-stranded is made double-stranded by the synthesis of complementary fragment 140. The resulting double-stranded portion will desirably include at least a binding protein recognition site 150. The length and exact nucleotides of the recognition sequence of recognition site 150 will depend upon the binding protein and recognition site of interest. For example, SP1 has a recognition sequence 6 nucleotides in length, Oct-1 has a recognition sequence 8 nucleotides in length, and NF-1 has a recognition sequence 15 nucleotides in length. The synthesis of the complementary fragment 140 can be accomplished by various means known in the art. For example, in embodiments such as those illustrated by FIG. 1(A)-1(C), where capture oligonucleotide 120 is attached at its 5' end to substrate 110, a DNA polymerase, such as the exo-Klenow fragment of DNA polymerase I, can be utilized to extend capture oligonucleotide 120 by creating complementary fragment 140 by incorporation of appropriate dNTPs, thus making target fragment 130 and recognition site 150 double-stranded.

Various means, such as a DNA ligase (e.g., Taq DNA Ligase), are used in certain embodiments to create a phosphodiester bond between the 3' hydroxyl termini and 5' phosphate termini of capture oligonucleotide 120 and complementary fragment 140. For other embodiments, such as those where capture oligonucleotide 120 is attached at its 3' end to substrate 110, complementary fragment 140 would be synthesized by other methods known in the art. For example, DNA primase, DNA polymerase δ, DNA ligase I, flap endonuclease 1, and Dna2 endonuclease can be utilized to create complementary fragment 140 when capture oligonucleotide 120 is attached at its 3' end. Embodiments utilizing this step of the assay to produce double-stranded nucleic acids may additionally include a step to remove extraneous single-stranded nucleic acids. This can be performed by various means in the art, such as utilizing exonuclease I to digest unbound fragments of nucleic acids from the sample and unbound capture oligonucleotides 120 through its 3' to 5' single-strand digestion in embodiments where capture oligonucleotides 120 are attached to substrate 110 at their 5' end. Other embodiments may utilize one or more washing steps after synthesis of complementary fragment 140 to remove unbound fragments of nucleic acids from the sample, in addition to other purposes, such as removing a target fragment 130 which did not completely hybridize with the complementary portion of capture oligonucleotide 120 because of sequence differences.

Additional embodiments may omit the step of synthesizing complementary fragment 140, and additional steps, such as the digestion of single-stranded nucleic acids, if the binding proteins of interest bind to single-stranded nucleic acids, such as Replication protein A, which binds to single-stranded DNA, or Polyadenylate-binding protein 1, which binds to mRNA. Other embodiments directed to binding proteins specific for single-stranded nucleic acids will still utilize the step of synthesizing complementary fragment 140. In these embodiments, target fragment 130 will be used to guide the proper synthesis of complementary fragment 140, wherein for these embodiments the desired recognition sequence of recognition site 150 is located within complementary fragment 140. After synthesis of complementary fragment 140 is complete, the resulting double-stranded oligonucleotide is separated so that target fragment 130 can be removed, thus making recognition site 150 on complementary fragment 140 available for subsequent binding by a binding protein 160. Separation of the double-stranded oligonucleotides can be accomplished by a variety of means known in the art, such as through thermal denaturation, or enzymatically through the use of, for example, a helicase.

Creation of complementary fragment 140 based upon the exact sequence of target fragment 130 provides important advantages to alternative methods of forming an array for the measurement of binding protein affinities, such as manufacturing arrays of double-stranded oligonucleotides and directly adding the binding proteins of interest. While target nucleic acid fragment 130 may be obtained from any desired source, including artificial synthesis, it is desirable in many embodiments to obtain the genomic sample to be assayed from the individual organism of interest, for instance, a human patient or a laboratory animal. Use of a particular individual organism to supply target fragments 130 allows creation of recognition sites 150 that are specific to the individual which supplied the sample. Thus, mutations within the sequence of recognition site 150, such as SNPs, insertions, deletions or inversions, which are present within the organism, will also be present within recognition site 150. Furthermore, this customization of the recognition sites 150 to be assayed with the binding proteins of interest does not require the creation of a custom array for each individual because it is not necessary to customize substrate 110 and capture oligonucleotides 120. Thus, capture oligonucleotides 120 may remain the same between two arrays of a particular assay type, even when two distinct individuals are being assayed, which simplifies manufacturing and lowers costs while still providing an assay that is customized to the particular individual of interest. This advantage is also present within embodiments directed to assaying binding affinities of single-stranded binding proteins and which do not utilize the creation of complementary fragment 140, as target fragment 130, which contains recognition site 150 in those embodiments, is still specific to the individual of interest in those embodiments. Additionally, the assay is not limited to recognition sites 150 of a particular size, as would be a case with a protein binding microarrays that contains, for example, all sequence variants of a particular size, such as 8mers or 10mers. For example, Nuclear factor I binds to a recognition sequence that is 15 nucleotides in length, and therefore such binding proteins could not be assayed with such a protein binding microarray.

FIG. 1(C) illustrates the subsequent step in certain embodiments of the assay. At least one binding protein 160 is introduced to substrate 110 and allowed to potentially bind to recognition site 150. The type and source of nucleic acid binding protein 160 will vary depending on the assay being performed. Embodiments focusing on common binding proteins can utilize commercially obtained binding proteins, such as the TATA-box binding protein (TBP) or p53 protein, available from, for example, Jena Bioscience GmbH (Jena, Germany). In some circumstances, binding proteins with mutations, such p53 proteins with specific mutations, may also be available commercially and be utilized to determine the differences in binding affinity of a mutant protein for a particular recognition site in relation to the wild type binding protein. However, obtaining binding proteins with all of the mutations desired for a particular assay may not always be possible or feasible. Furthermore, embodiments of the assay utilizing binding proteins specific to the particular individual organism of interest can provide a significant advantage in determining more accurate binding affinities, especially when these embodiments utilize target fragments 130 that are also specific to the individual. A combination of binding proteins 160 and target fragments 130 that are specific to the individual creates an assay that is entirely specific to the individual while being of a common design, with the one or more substrates 110 with the common and pre-designed capture oligonucleotides 120. Binding proteins specific to an individual can be acquired through various means known in the art, such as through in vitro translation of recombinant proteins utilizing plasmid DNA or PCR products with lysates of required translational machinery components from, for example, *Escherichia coli*. Other methods known in the art can also be utilized for production of desired binding proteins, for example, in vivo expression techniques that may, for instance, transform cells with plasmid DNA, cultivating and lysing transformed cells, and purifying the desired proteins. Translation of proteins through in vitro techniques is possible with commercially available kits, such as the EasyXpress Protein Synthesis Kit (Qiagen, Inc., Valencia, Calif.). Such techniques facilitate the production in vitro of, for example, a particular patient's binding proteins, with any mutations that may be present, for further analysis within the assay. This allows not only for customization of the binding proteins within the assay to an individual, but also the use of mutant variants of binding proteins that are rare or previously unknown, and that would otherwise not be available. Such embodiments of the assay utilizing recognition sites 150 and binding proteins 160 that are specific to the individual of interest allow measurement of the binding affinities of interest on a level that is more specific than other available assays, and can allow the detection of genetic disorders and the diagnosis of medical conditions when knowledge of the mutation within the recognition site and/or the binding protein alone is insufficient. Assays that are personalized with respect to only the recognition sites or the binding proteins of interest will not always detect and/or properly measure changes in binding affinity, especially in situations where both the recognition sequence at issue and the binding domain of the protein at issue both contain one or more mutations.

Recombinant protein production also provides the ability to use a plurality of mutant forms of a particular binding protein within embodiments of the assay. Embodiments may utilize this ability in various ways, such as the creation of multiple mutant variants of a binding protein to compare their associated binding affinities with one or more recognition sites. Creation of mutant forms of binding proteins is also useful for a variety of research purposes, such as, for example, the creation of modified artificial transcription factors in therapeutic gene modulation research that seeks to alter the expression of a particular gene or pathway. Embodiments of the assay utilize multiple mutant forms of a binding protein to measure their relative binding affinities with one or more recognition sites 150, with one or more possible recognition sequences for each recognition site. Such assays can be particularly useful, for example, in measuring the differences in the binding affinity of various mutant versions of a binding protein that are present in a population for the various mutant versions of its corresponding recognition site that are also present in the population, and allowing such measurements without having to find individuals possessing all of the mutant versions.

FIG. 1(C) illustrates an embodiment where binding protein 160 comprises a label 170. Label 170 may be any suitable label known in the art. Label 170 may be, for example, a fluorescent label, such as an organic dye (e.g., fluorescein, Cy3, Cy5, rhoadamine), a biological fluorophore (e.g., phycoerythrocyanin), or a quantum dot (e.g., a carboxyl quantum dot). Fluorescent labels may include, for example, N-hydroxysuccinimide ester activated dyes that react with exposed amino groups, malemide activated dyes that react with sulfhydryl groups, phosphine activated dyes that react with azide groups, or other suitable labels known in the art. Depending on the embodiment, suitable labels may be available commercially from, for example, Invitrogen (Carlsbad, Calif.), Thermo Fisher Scientific (Waltham, Mass.), and ATTO-TEC GmbH (Siegen, Germany). Depending on the embodiment, a variety of fluorescent labels with different excitation and emission characteristics can be utilized with the various binding proteins 160 of the assay. For example, an exemplary assay may have one or more types of binding proteins labeled with different fluorescent labels, each producing different emission colors, such as non-limiting examples of blue, green, yellow, orange and red (and/or multiple shades of one or more of these colors and their respective emission spectra). Furthermore, in some embodiments, a binding protein 160 may have a combination of dyes to produce a distinct fluorescent profile for a particular binding protein 160 within the assay. Depending on the number and variety of binding proteins 160, the number and variety of recognition sites 150 and their binding suitability with respect to the binding proteins 160 that will be present, the preferred label or labels to be utilized, and other assay characteristics of the particular embodiment, labeling may be performed before binding proteins 160 are introduced within the assay, during binding, or subsequent to binding. The labeling of binding proteins 160 may occur in a single step, or within multiple steps (e.g., single labeling step of labeled antibodies appropriate for the binding proteins at issue, sandwich labeling with labeling molecular pairs such as biotin and streptavidin, etc.). Embodiments may utilize various procedures known in the art to optimize detection and proper measurement of bound binding proteins and their associated labels, such as washing to remove unbound binding proteins. As well, some embodiments may use additional fluorescent labels within the assay for the purposes of, for example, imaging calibration, background controls, normalization, or minimizing the effects of hybridization variation. These additional labels may be incorporated within the assay through, for example, capture oligonucleotide 120, target fragment 130, complementary fragment 140, or binding protein 160. Detection of fluorescent labels may be accomplished in embodiments of the assay through a variety of methods utilizing suitable instruments known in the art. These include, for example, scanning methods and systems as described in U.S. Pat. Nos. 5,143,854; 5,578,832; 5,631,734; 5,834,758; 5,936,324; 5,981,956; 6,025,601; 6,141,096; 6,185,030; 6,201,639; 6,490,533; 6,643,015; 6,650,411; 6,741,344; 6,813,567; 7,095,032; 7,062,092; 7,148,492; 7,222,025; 7,312,919; 7,317,415; 7,406,391; 7,682,782; and 7,689,022; each of which is hereby incorporated by reference in its entirety for all purposes.

Detection of the resulting intensity level of a fluorescent label provides, at least in part, a measurement of the affinity between the one or more binding proteins 160 labeled with that particular label 170 for the one or more recognition sites 150 created through the corresponding capture oligonucleotides 120, target fragments 130 and complementary fragments 140. Both absolute and relative quantification of labeling, fluorescent or otherwise (e.g. $^{32}$P or $^{125}$I labeling), is well known in the art. See, e.g., Yan and Marriott, "Analysis of protein interactions using fluorescence technologies," Current Opinion in Chemical Biology, 7: 635-640 (2003); Haab et al., "Protein microarrays for highly parallel detection and quantitation of specific proteins and antibodies in complex solutions," Genome Biology, 2(2): research0004.1-0004.13 (2001); and Ge, "UPA, a universal protein array system for quantitative detection of protein-protein, protein-DNA, protein-RNA and protein-ligand interactions," Nucleic Acids Research, 28(2): e3, i-vii (2000). Relative quantifications can be especially useful within embodiments utilizing two or more variants of a binding protein, or related binding proteins, such as a wild type variant of a binding protein and one or more mutant variants of the same protein. In such embodiments, each variant could possess, for instance, a distinguishable label in order to construct a comparison of the relative binding affinities of each binding protein variant for a particular recognition site 150 by measuring and comparing the signal intensities for each variant (e.g., comparing signal intensity ratios for one binding protein variant relative to another binding protein variant).

Additional processing, such as normalization of signal intensities and background calibration, can further refine the measured signal intensities into measurements of binding affinity. Further refinement may be possible by other techniques, such as incorporation of particular fluorescent label(s) into capture oligonucleotides 120, target fragments 130, complementary fragments 140, and/or binding proteins 160 for the purposes of normalization, background, use as controls, or other use of the resulting intensity values in order to account for variations within the assay of the one or more labels 170. For example, depending on the assay design, the various target fragments 130 may have slightly different hybridization kinetics with respect to their corresponding capture oligonucleotides 120. Accordingly, different features of an array may have slight relative differences in the quantities of target fragments 130 bound to their respective capture oligonucleotides 120. These differences can then affect the resulting signals from labels 170 associated with binding proteins 160. Therefore, normalization and other techniques to even out or otherwise account for these differences can positively influence the eventual data utilized in assessing the relevant binding protein affinities.

Other suitable methods of labeling, either directly or indirectly, are also possible according to embodiments of the assay. For example, label 170 may also be an antibody, with an associated label or tag to be utilized with the antibody to enable detection, such as a radioisotope, enzymatic tag (e.g., horseradish peroxidase), or a fluorescent tag (e.g., utilizing a biotin labeled antibody with subsequent use of streptavidin). While antibodies are not required for labeling and detection of binding protein 160, they may be convenient depending on the binding proteins of interest and availability of suitable antibodies. For example, if a common binding protein is of interest, labeled specific antibodies for that protein may be readily available. Other known labeling features are also possible in various embodiments, such as the use of a fluorescent dye in combination with a labeled antibody (e.g., labeling a protein with sulforhodamine 101 acid chloride and utilizing labeled antibodies which recognize that fluorophore). Regardless of the manner of labeling employed, however, an important feature of the various embodiments is that the entire assay can be personalized to an individual of interest while also allowing the assay to be performed entirely in vitro. This allows in vivo steps to be omitted, and that are otherwise required in other techniques, such as those involving chromatin immunoprecipitation.

While FIG. 1(A)-1(C) depict a single capture oligonucleotide 120 attached to a single substrate 110, and the use of a single binding protein 160, it should be appreciated that each of these elements will be present in multiplicative form in various embodiments. For example, while some embodiments may utilize a single substrate 110 which possesses one or more capture oligonucleotides 120, other assay embodiments utilize multiple substrates 110. For example, embodiments may use beads, microspheres or microparticles as substrate 110, and which may number, for example, from a single substrate to thousands or millions depending on the particular design of the assay. Each substrate 110 may possess a single capture oligonucleotide 120, multiple copies of a single capture oligonucleotide 120, one copy each of a plurality of capture oligonucleotides 120, or multiple copies of multiple different capture oligonucleotides 120. In this manner, embodiments of the assay are able to capture one or more target fragments 130 with one or more substrates 110. For instance, a substrate 110, or a combination of substrates 110, may possess twenty copies of the a particular capture oligonucleotide 120, such that up to twenty target fragments 130 all containing the same recognition site 150 are captured onto substrate 110. Subsequently, one or more of the corresponding binding protein 160 variants (e.g., the wild type binding protein and one or more mutant versions of the binding protein, or a selection of wild and mutant variants from within a family of binding proteins) are introduced to substrate 110. Detection of the one or more types of utilized labels 170 can then provide information regarding the binding affinities of the different variants of the binding protein 160 with respect to recognition site 150. Embodiments of the assay further envision combining this binding affinity information with information about the precise sequence of the one or more recognition sites 150, obtained by various means known in the art, such as, for example, sequencing by hybridization, chain-termination sequencing, dye-terminator sequencing, massively parallel signature sequencing, Polony sequencing, pyrosequencing, reversible dye-terminator sequencing, sequencing by ligation, ion semiconductor sequencing, or unchained sequencing by ligation of nucleic acid nanoballs. Combining the obtained information facilitates the analysis of the binding affinity of multiple different binding proteins (and mutant variants thereof) with the exact recognition sequences of the relevant recognition sites, with all the data entirely personalized to the individual of interest. This can be particularly advantageous when an individual is suffering from a condition or disease that may result from one or more mutations within the recognition sequence of a recognition site 150, and which also results from one or more mutations within the binding protein 160 which affect the protein's binding ability with its normal corresponding recognition sequence.

Furthermore, while FIG. 1(A)-1(C) depict a single binding protein 160 involved with recognition site 150, some embodiments of the assay are directed to the measurement of binding affinities of binding proteins which operate in association with other cellular molecules, such as regulatory proteins, transcription cofactors or miRNAs. For example, the transcription factor Mcm1 interacts with, depending on the cell type and genes at issue, the cofactors $\alpha 1$, $\alpha 2$, and Ste12. Mcm1 forms a complex with $\mu 1$ alone, with both $\mu 1$ and $\alpha 2$ simultaneously, or with Ste12 alone depending on the cell type and genes at issue. Thus, embodiments of the assay will utilize a particular binding protein 160 with one or more associated molecules affecting its binding activity, such as transcription cofactors or miRNAs. Such embodiments facilitate the comparative measurement of the affinity of a binding protein 160 for one or more recognition sites 150 when the assay is performed with one or more cofactors to enable, for example, the measurement of the binding affinity when the binding protein 160 is complexed with one cofactor in comparison to being complexed with another cofactor. Furthermore, certain embodiments will introduce one or more mutations within binding protein 160 or these associated proteins so that the binding affinity of the resulting complex or otherwise altered binding protein 160 can be accurately measured with respect to the recognition site 150 at issue. As with binding protein 160, these other proteins may be specific to the individual of interest and are acquired through suitable in vitro or in vivo techniques to preserve any possibly relevant mutations so that the effect of the mutations will be incorporated within the assay. Additionally, embodiments incorporating molecules associated with binding protein 160 and which may subsequently affect the binding affinity for recognition site 150 may further include one or more labels 170 associated with one or more components of the combined binding complex. For example, a binding protein 160 and a cofactor protein may be labeled in a florescence resonance energy transfer (FRET) manner, where, for instance, either the binding protein 160 or the cofactor protein is labeled with a donor dye and the other molecule is labeled with the acceptor dye. Subsequent binding of the binding protein 160 and the cofactor protein, and detection of the acceptor emission upon donor excitation, allows detection of the protein complex. Non-limiting examples of FRET pairs are Cy2-Cy3 or Cy3-Cy5. Some embodiments may incorporate fluorescent proteins into proteins utilized within the assay, for example variants of green fluorescent protein such as cyan fluorescent protein utilized with yellow fluorescent protein.

Figure 2C:
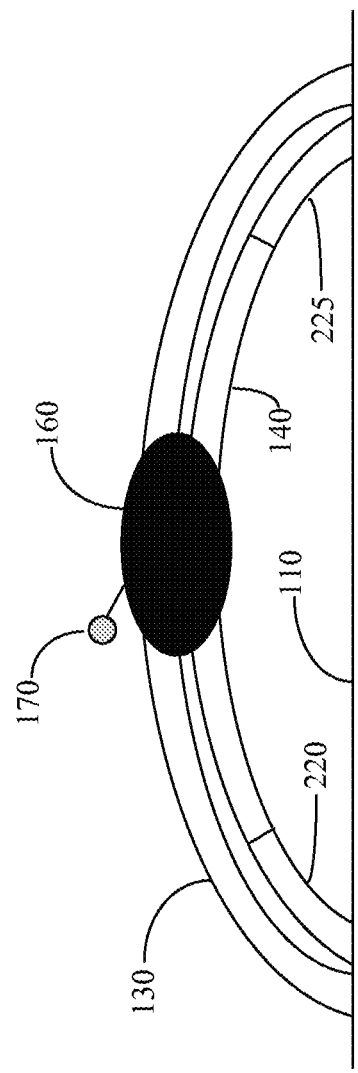
FIG. 2(C) illustrates a non-limiting example of binding of a labeled binding protein to the double-stranded binding site formed in FIG. 2(B).

Additional aspects of certain embodiments of the assay are illustrated by FIG. 2(A)-2(C). These embodiments utilize an approach partially based upon molecular inversion probe (MIP) technology. Various aspects of MIP technology are described in, for example, Hardenbol et al., "Multiplexed genotyping with sequence-tagged molecular inversion probes," Nature Biotechnology, 21(6): 673-678 (2003); Hardenbol et al., "Highly multiplexed molecular inversion probe genotyping: Over 10,000 targeted SNPs genotyped in a single tube assay," Genome Research, 15: 269-275 (2005); Burmester et al., "DMET microarray technology for pharmacogenomics-based personalized medicine," Methods in Molecular Biology, 632: 99-124 (2010); Sissung et al., "Clinical pharmacology and pharmacogenetics in a genomics era: the DMET platform," Pharmacogenomics, 11(1): 89-103 (2010); Deeken, "The Affymetrix DMET platform and pharmacogenetics in drug development," Current Opinion in Molecular Therapeutics, 11(3): 260-268 (2009); Wang et al., "High quality copy number and genotype data from FFPE samples using Molecular Inversion Probe (MIP) microarrays," BMC Medical Genomics, 2:8 (2009); Wang et al., "Analysis of molecular inversion probe performance for allele copy number determination," Genome Biology, 8(11): R246 (2007); Ji et al., "Molecular inversion probe analysis of gene copy alternations reveals distinct categories of colorectal carcinoma," Cancer Research, 66(16): 7910-7919 (2006); and Wang et al., "Allele quantification using molecular inversion probes (MIP)," Nucleic Acids Research, 33(21): e183 (2005), each of which is hereby incorporated by reference in its entirety for all purposes. See also in U.S. Pat. Nos. 6,858,412; 5,817,921; 6,558,928; 7,320,860; 7,351,528; 5,866,337; 6,027,889 and 6,852,487, each of which is hereby incorporated by reference in its entirety for all purposes.

MIP technology has previously been successfully applied to other areas of research, including the novel identification and subclassification of biomarkers in cancers. See, e.g., Brewster et al., "Copy number imbalances between screen- and symptom-detected breast cancers and impact on disease-free survival," Cancer Prevention Research, 4(10): 1609-1616 (2011); Geiersbach et al., "Unknown partner for USP6 and unusual SS18 rearrangement detected by fluorescence in situ hybridization in a solid aneurysmal bone cyst," Cancer Genetics, 204(4): 195-202 (2011); Schiffman et al., "Oncogenic BRAF mutation with CDKN2A inactivation is characteristic of a subset of pediatric malignant astrocytomas," Cancer Research, 70(2): 512-519 (2010); Schiffman et al., "Molecular inversion probes reveal patterns of 9p21 deletion and copy number aberrations in childhood leukemia," Cancer Genetics and Cytogenetics, 193(1): 9-18 (2009); Press et al., "Ovarian carcinomas with genetic and epigenetic BRCA1 loss have distinct molecular abnormalities," BMC Cancer, 8:17 (2008); and Deeken et al., "A pharmacogenetic study of docetaxel and thalidomide in patients with castration-resistant prostate cancer using the DMET genotyping platform," Pharmacogenomics, 10(3): 191-199 (2009), ach of which is hereby incorporated by reference in its entirety for all purposes.

MIP technology has also been applied to the identification of new drug-related biomarkers. See, e.g., Caldwell et al., "CYP4F2 genetic variant alters required warfarin dose," Blood, 111(8): 4106-4112 (2008); and McDonald et al., "CYP4F2 Is a Vitamin $K_1$ Oxidase: An Explanation for Altered Warfarin Dose in Carriers of the V433M Variant," Molecular Pharmacology, 75: 1337-1346 (2009), each of which is hereby incorporated by reference in its entirety for all purposes. Other MIP applications include drug development and safety research. See, e.g., Mega et al., "Cytochrome P-450 Polymorphisms and Response to Clopidogrel," New England Journal of Medicine, 360(4): 354-362 (2009); Dumaual et al., "Comprehensive assessment of metabolic enzyme and transporter genes using the Affymetrix Targeted Genotyping System," Pharmacogenomics, 8(3): 293-305 (2007); and Daly et al., "Multiplex assay for comprehensive genotyping of genes involved in drug metabolism, excretion, and transport," Clinical Chemistry, 53(7): 1222-1230 (2007), each of which is hereby incorporated by reference in its entirety for all purposes. Further applications of MIP technology include genotype and phenotype databasing. See, e.g., Man et al., "Genetic Variation in Metabolizing Enzyme and Transporter Genes: Comprehensive Assessment in 3 Major East Asian Subpopulations With Comparison to Caucasians and Africans," Journal of Clinical Pharmacology, 50(8): 929-940 (2010), which is hereby incorporated by reference in its entirety for all purposes.

FIG. 2(A)-2(C) illustrate a non-limiting example of certain embodiments utilizing an approach which utilizes the aspect of two capture oligonucleotides for a single target in combination with a gap fill reaction to complete a double-stranded nucleic acid for further use. Many aspects of the embodiments illustrated by FIG. 2(A)-2(C), however, will be similar with respect to the embodiments illustrated by FIG. 1(A)-1(C). A second non-limiting example of a different MIP variation is illustrated within FIGS. 4(A)-4(D) and 5(A)-5(C).

In FIG. 2(A), a first capture oligonucleotide 220 and a second capture oligonucleotide 225 are attached to substrate 110. First and second capture oligonucleotides 220 and 225 can be attached to substrate 110 at their 5' and 3' ends, respectively, or in the reverse configuration, depending on the particular assay configuration and embodiment. As described earlier with respect to capture oligonucleotide 120, first and second capture oligonucleotides 220 and 225 may be synthesized or attached (after synthesis) to substrate 110 through any suitable method and may comprise any suitable number of nucleotides. At least a portion of first capture oligonucleotide 220 is complementary to a first region of target fragment 130, while at least a portion of second capture oligonucleotide 225 is complementary to a second region of target fragment 230. FIG. 2(A)-2(C) depict an embodiment where the entirety of first capture oligonucleotide 220 and second capture oligonucleotide 225 is complementary to a first region of target fragment 130 and a second region of target fragment 130, respectively. In other embodiments, one or more nucleotides of first and second capture oligonucleotides 220 and 225 may not be complementary to the first and second regions of target fragment 130, respectively. The one or more non-complementary nucleotides may be, for example, nucleotides utilized as a linker or spacer between substrate 110 and the portions of first and second capture oligonucleotides 220 and 225 that are complementary to regions of target fragment 130. Depending on the embodiment of the assay and the location of recognition site 150, one or both of capture oligonucleotides 220 and 225 may be unique sequences. Additionally, in some embodiments, one or both of capture oligonucleotides 220 and 225 may be unique, conserved sequences. However, in other embodiments, neither first capture oligonucleotide 220 nor second capture oligonucleotide 225 is a unique or conserved sequence. In a situation where neither of the capture oligonucleotides 220 and 225 are unique, capture of the desired target fragment 130 is accomplished by, for example, selection of the sequences for the first and second capture oligonucleotides such that the combination of the two oligonucleotide sequences and the distance between them is unique for the desired sample, or at least the desired sample as prepared and processed (e.g., after selective amplification). In some embodiments, one of capture oligonucleotides 220 and 225 corresponds to an adaptor sequence, wherein the corresponding complementary adaptor sequence has been added to target fragment 130. As depicted in FIG. 2(B), first capture oligonucleotide 220 is downstream of the recognition site 150 of interest while second capture oligonucleotide 225 is upstream of the recognition site 150 of interest, both with respect to target fragment 130, but it should be appreciated that in other embodiments the orientation can be reversed.

FIG. 2(B) illustrates the next step in certain embodiments of the assay, where target fragment 130 is made double-stranded by the synthesis of complementary portion 140. The resulting double-stranded portion will include at least recognition site 150. This can be accomplished by various means known in the art, such as for example, enzymatically via a DNA polymerase and a DNA ligase, such as the exo-Klenow fragment of DNA polymerase I and Taq DNA ligase. In some embodiments, if a DNA polymerase is utilized, the free 3' end of first or second capture oligonucleotide 220 or 225 (depending on the respective orientations of each with respect to substrate 110) is extended until the 5' end of the other capture oligonucleotide 220/225 is reached, and an appropriate DNA ligase is then utilized to join the strands. Also, as before, embodiments may utilize additional steps, such as removing extraneous nucleic acids with, for example, exonuclease I to remove single-stranded DNA from the assay. Furthermore, embodiments utilizing first and second capture oligonucleotides 220 and 225 may also omit the step of synthesizing complementary fragment 140 if the binding proteins 160 of interest bind to single-stranded nucleic acids and recognition site 150 is located on target fragment 130.

FIG. 2(C) illustrates the subsequent step in certain embodiments of the assay, and is quite similar to the described embodiments associated with FIG. 1(C), as the primary difference in the assay at this step is that the double-stranded oligonucleotide containing recognition site 150 in this embodiment is attached to substrate 110 at both ends while in the embodiments depicted in FIG. 1(C), the oligonucleotide is only attached to substrate 110 at one end.

Other embodiments utilize other variations of MIP technology approach, such as where a single MIP polynucleotide probe is employed in-solution to facilitate selective amplification of one or more regions of interest within a sample of nucleic acids before those selected regions are subsequently utilized as target fragments 130 in a binding protein affinity assay. Such variations of MIP technology are described within, for example, the earlier referenced patents and non-patent literature relating to MIP technology and its applications within the novel identification and subclassification of biomarkers in cancers, the identification of new drug-related biomarkers, genotype and phenotype databasing, and other applications.

Figure 3:
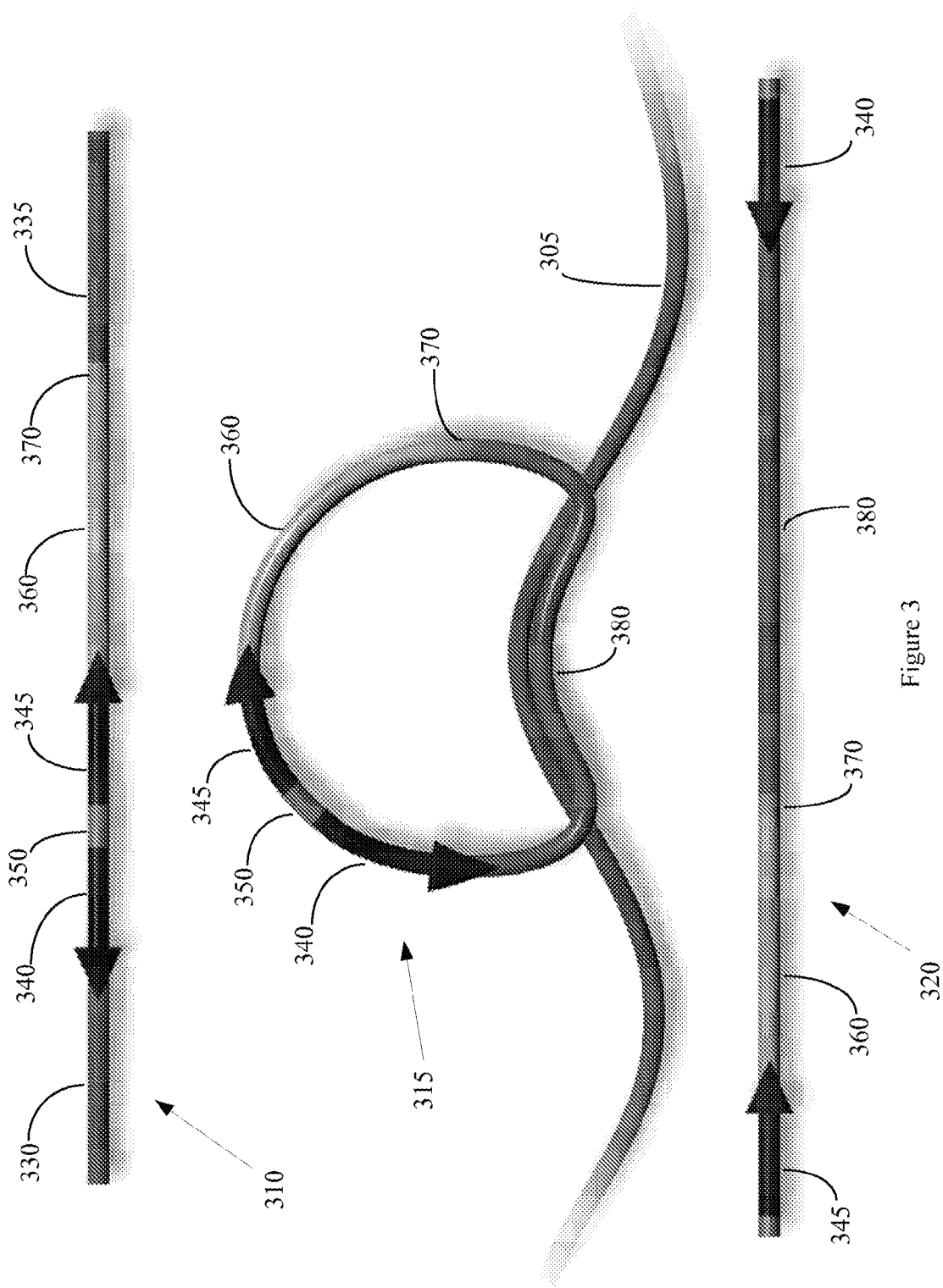
FIG. 3 illustrates a non-limiting example of Molecular Inversion Probe (MIP) technology as utilized within a MIP probe that begins in a linear form, is circularized after hybridization to a target nucleic acid, and is subsequently linearized.

A non-limiting example of such a MIP probe and its structure during the assay is illustrated within FIG. 3. A nucleic acid of interest 305 is the target for a MIP probe. MIP probe 310 illustrates a non-limiting example of the initial, starting form of the MIP probe that is added to the sample containing nucleic acid 305. MIP probe 315 is the circularized version of MIP probe 310 after hybridization with nucleic acid 305. MIP probe 320 is the subsequent linearized version of circularized MIP probe 315.

MIP probe 310 comprises several components, including a first genomic homology region 330 and a second genomic homology region 335. First and second genomic homology regions 330 and 335 are complementary to different portions of nucleic acid 305. These different portions of nucleic acid 305 can be directly adjacent (e.g., without any intervening bases), or separated by one or more bases (e.g., separated by a known SNP site, separated by a recognition site 150). Thus, when the complementary portions of nucleic acid 305 are separated by one or more bases, first and second genomic homology regions 330 and 335 will also be separated when the assay begins to convert MIP probe 310 into circularized MIP probe 315, starting by hybridizing the first and second genomic homology regions 330 and 335 of MIP probe 310 to nucleic acid 305. This separation, or gap, within MIP probe 315 is then filled by adding an appropriate base or bases and a polymerase to the assay solution, which will add bases to the 3' end of MIP probe 315. The circularization and conversion of MIP probe 310 into MIP probe 315 is then completed through the use of an appropriate ligase. Thus, first and second genomic homology regions 330 and 335, which begin within MIP probe 310 at opposite ends of the probe, become joined together to form combined genomic homology region 380 of MIP probe 315. If first and second genomic homology regions 330 and 335 were separated by one or more bases after hybridization to nucleic acid 305, then combined genomic homology region 380 will additionally include the bases which were added to fill the gap. After circularization of the MIP probes with their respective targets within the sample, the remaining nucleic acids that are present (e.g., non-circularized MIP probes and any remaining linear nucleic acids from the sample), can be removed through any suitable method, such as the use of an appropriate exonuclease (e.g., Exo I).

Certain assay embodiments utilizing MIP probes do not employ an amplification step, and instead utilize the inherent high specificity of MIP probes for their targets (due to the requirement that two hybridization events must occur between a particular probe and a region of a nucleic acid within the sample at issue). Other assays, however, do utilize one or more amplification steps. This can occur utilizing circularized MIP probe 315 through, for example, use of rolling circle replication, or can occur through traditional PCR after linearization of circularized MIP probe 315 to produce linearized MIP probe 320. Within assays that perform amplification after linearization of circularized MIP probe 315, many embodiments utilize a MIP probe 310 that additionally comprises a first primer binding site 340 and a second primer binding site 345. First and second primer binding sites 340 and 345 can function, for example, as forward and reverse PCR primer sites for linearized MIP probe 320. In certain embodiments, these PCR primer sites are complementary to a set of universal primers such that a plurality of different MIP probes associated with a plurality of nucleic acids of interest each incorporate these universal primer sites, and therefore facilitate amplification of all MIP probes (that are circularized into MIP probes 315 and subsequently linearized into MIP probes 320) with as few as a single set of PCR primers. Thus, increasing the number of different MIP probes utilized within a particular assay can facilitate a high level of multiplexing within the assay at issue.

MIP probe 310 may further comprise a cleavage site 350. Cleavage site 350 facilitates the cleavage of circularized MIP probe 315 to re-linearize the probe and form MIP probe 320. Cleavage site 350 may be a restriction site for an appropriate enzyme, but may also employ other mechanisms to allow selective cleavage. For example, cleavage site 350 may comprise one or more uracil bases to allow cleavage of circularized MIP probe 315 through incubation with Uracil-DNA glycosylase to create one or more abasic sites for subsequent cleavage through an appropriate means (e.g., heat, an endonuclease that cleaves at abasic sites). Other mechanisms, such as the use of other modified bases and enzymes specific for those modified bases, and which will create the abasic site and cleave the MIP probe, are also possible. Alternatively, a separate enzyme or mechanism (e.g., high temperature incubation) can be used to cleave the MIP probe at the created abasic sites. While the particular embodiment illustrated within FIG. 3 contains only one cleavage site 350, other embodiments may use two or more cleavage sites 350 as may be required or desirable for an assay. The particular embodiment illustrated within FIG. 3 positions cleavage site 350 between first and second primer binding sites 340 and 345. This positioning results in a linearized MIP probe 320 that place the first and second primer binding sites 340 and 345 on opposite ends of the probe, thus facilitating their use as forward and reverse primer binding sites for PCR.

MIP probe 310 may additionally comprise a tag sequence 360. Tag sequence 360 can comprise, for example, a unique sequence of nucleotides (unique within the assay at issue) in order to provide a unique barcode for the MIP probe and any resulting amplicons which incorporate that particular tag sequence 360 from MIP probes that are circularized into MIP probes 315 and then subsequently linearized into MIP probes 320. While the MIP probe 310 illustrated within FIG. 3 only incorporates one tag sequence 360, other embodiments may incorporate two or more tag sequences 360. For instance, a variation of MIP probe 310 can incorporate two different tag sequences 360 in order to provide two unique sequences for subsequent use within the assay to identify or correspond to various aspects (e.g., the target sequence of nucleic acid 305, the sample within the assay to which MIP probe 310 was added). The one or more tag sequences 360 of linearized MIP probe 320 can be subsequently utilized in a variety of means known in the art, including but not limited to hybridization with nucleic acid probes on a microarray (e.g., a microarray with oligonucleotide probes complementary to tag sequence 360 and/or its complement created within amplification), sequencing, real-time PCR, digital PCR, etc. Certain variations of tag sequences 360, such as those which will be hybridized with a microarray, comprise a sequence that, when considered in the context of all of the tag sequences 360 at issue within an assay from the different MIP probes 310 which are utilized, will maximize the mismatch between any pair of tag sequences 360 in order to minimize cross-hybridization.

MIP probe 310 may also comprise a restriction site 370. Restriction site 370 can comprise, for example, a sequence recognized by a restriction enzyme. Incorporation of restriction site 370 allows, within certain embodiments, the relevant sequence to be incorporated within the amplicons (assuming the embodiment utilizes amplification). The amplicons can be maintained in double-stranded form if the restriction site 370 is for a restriction enzyme that recognizes and digests a double-stranded recognition site, or the strands of the amplicons can be separated for use with a restriction enzyme that digests a single-stranded site. Even within assays that do not utilize amplification, restriction site 370 can still be included within MIP probe 310 and subsequently utilized. Restriction site 370 can be used for a variety of purposes in different assays, including but not limited to separation of tag sequence 360 from combined genomic homology region 380. For example, if a particular assay utilizes a tag microarray for detection of tag sequences 360, restriction site 370 and its corresponding restriction enzyme can be utilized to separate tag sequence 360 from combined genomic homology region 380 before hybridization to the array. Preferably, the restriction site 370 possesses a sequence that occurs infrequently to aid in avoiding its occurrence within the MIP probes within the assay at issue (e.g., to avoid having the sequence of restriction site 370 occur in the first or second genomic homology regions 330 and 335. As with tag sequence 360, certain embodiments may incorporate two or more restriction sites 370 as may be necessary or desirable within particular assays. Other embodiments of MIP probes may utilize only a portion of these described features, and in different quantities and/or for different functions.

FIGS. 4(A)-4(D) and 5(A)-5(C) illustrate a non-limiting embodiment utilizing certain embodiments of MIP probes, such as those described above and illustrated within FIG. 3, within a binding protein affinity assay. In these embodiments, MIP probes are used to selectively capture, and optionally amplify, target fragments 130 before hybridization to capture oligonucleotides 120.

FIG. 4(A) illustrates a non-limiting embodiment of the initial, starting form of the MIP probe 410 that is added to the sample containing target fragment 130. In the particular illustrated embodiment, MIP probe 410 comprises first and second genomic homology regions 330 and 335, first and second primer binding sites 340 and 345, cleavage site 350, tag sequence 360, and restriction site 370. As described above for FIG. 3, certain embodiments may omit one or more of these features. For example, if amplification of the circularized MIP probe is not going to be performed, then first and second primer binding sites 340 and 345 are unnecessary. Alternatively, if tag sequence 360 will not be utilized within the assay (e.g., a microarray with probes containing complementary sequences to the tags will not be used), then tag sequence 360 can be omitted. In other variations in which tag sequence 360 is included and utilized, the tag sequence 360 is not separated from combined genomic homology region 380, and thus restriction site 370 may thus be unnecessary in such embodiments.

FIG. 4(B) illustrates a non-limiting example of MIP probe 410 after hybridization with target fragment 130, thus creating partially circularized MIP probe 415. First and second genomic homology regions 330 and 335 have hybridized to the portions of target fragment 130 for which they are respectively complementary. As depicted within FIG. 4(B), there is a gap between first and second genomic homology regions 330 and 335. The size of the gap can vary depending on the embodiment and also the target fragment 130 (and its relevant recognition site 150) at issue. For example, if a purpose of the overall assay at issue is to customize the sequence of the recognition sites 150 to the particular individual (e.g., a human patient being tested for their particular affinities to different binding proteins as a precursor to the determination of a treatment path), then the gap desirably includes the recognition site 150 at issue. Accordingly, if the individual possesses one or more mutations affecting recognition site 150 (e.g., SNP(s)), then those mutations and their corresponding effects on binding protein affinities will be accounted for in the assay.

Other embodiments, however, may use a smaller gap that only includes a portion of the recognition site 150 at issue, which in certain embodiments may translate to a gap of a single nucleotide. Smaller gaps may be utilized within embodiments that seek to test the affinity of binding proteins with respect to known SNPs within the recognition sites 150. For instance, if a recognition site 150 is known to have a particular SNP location, the corresponding first and second genomic homology regions 330 and 335 can be designed to leave a gap corresponding to at least that location within target fragment 130. Thereafter, the resulting gap can be filled in the circularization of MIP probe 415 by addition of the appropriate complementary base. Thus, the gap between first and second genomic homology regions 330 and 335 may need to be different for each recognition site 150 at issue within an assay, with the corresponding design of each MIP probe 410 reflecting those differences. For instance, in contrast to the situation described above with a recognition site 150 being known to include a SNP location, the same assay may also involve a second recognition site 150 that is known to include two SNP locations. The first and second genomic homology regions 330 and 335 for the MIP probe 410 utilized for this second recognition site would require a larger gap, in comparison to a possible gap of a single base with respect to a single SNP location, if the assay is to be customized to the particular genetic composition of the individual at issue.

FIG. 4(C) illustrates a non-limiting embodiment in which MIP probe 420 has been circularized from MIP probe 415 by the addition of one or more bases 385 to fill the gap between first and second genomic homology regions 330 and 335, thus creating combined genomic homology region 380 after appropriate ligation.

FIG. 4(D) illustrates a non-limiting embodiment of linearized MIP probe 425 after separation of MIP probe 420 from target fragment 130, and appropriate cleavage of MIP probe 420 at cleavage site 350. As a non-limiting example, cleavage site 350 can comprise three uracil bases, thus facilitating linearization of MIP probe 420 after treatment with uracil DNA glycosylase and endonuclease IV. The particular embodiment illustrated in FIG. 4(D) comprises first and second primer binding sites 340 and 345, which after linearization of MIP probe 420 can be utilized as forward and reverse PCR primer binding sites. If the sequences utilized for first and second primer binding sites 340 and 345 are employed for all MIP probes 410 included with a particular assay, then a single set of universal primers may be employed for multiplex amplification of all MIP probes 425 at issue. Alternatively, the use of multiple sets of primers can be employed with two or more sets of first and second primer binding sites 340 and 345 to facilitate selective amplification of MIP probes 425.

Additionally, the embodiment depicted in FIG. 4(D) contains a restriction site 370 between tag sequence 360 and combined genomic homology region 380. Use of an appropriate restriction enzyme for restriction site 370 can be employed to separate tag sequence 360 and combined genomic homology region 380 for subsequent use (e.g., hybridization of combined genomic homology region 380 with capture oligonucleotide 120). Alternatively, if tag sequence 360 will not be utilized within a particular assay, the MIP probes 410 can omit tag sequence and/or restriction site 370 from their design.

Figure 5A:
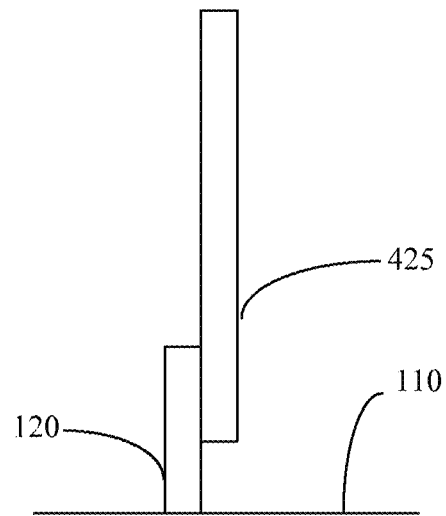
Figure 5B:
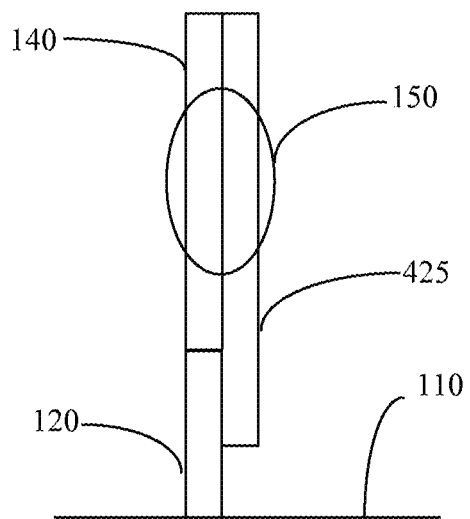

FIG. 5(A)-5(C) illustrate a non-limiting embodiment of subsequent use of linearized MIP probes 425 (and/or the complementary sequence that can be amplified within the MIP assay) in a binding protein affinity assay. At this point within the assay, the MIP embodiment variants are similar in many respects to the non-limiting embodiments illustrated and described within FIGS. 1(A)-1(C) and 2(A)-2(C). FIG. 5(A) depicts a non-limiting embodiment of MIP probe 425 hybridizing with a portion of capture oligonucleotide 120, which is attached to substrate 110. The portion of MIP probe 425 to which capture oligonucleotide 120 hybridizes will depend on the embodiment and the particular probes and capture oligonucleotides at issue. For example, in embodiments where a tag sequence 360 is utilized, all or a portion of capture oligonucleotide 120 can be designed to be complementary to all or a portion of the tag sequence 360. Alternatively, other embodiments omit tag sequence 360 (or separate tag sequence 360 from the rest of MIP probe 425 after appropriate cutting at restriction site 370), and thus hybridize a portion or all of capture oligonucleotide 120 with a portion of, for instance, combined genomic homology region 380.

As with earlier described embodiments, when the assay at issue is to be customized to the individual at issue who provided the relevant sample, capture oligonucleotide 120 hybridizes to MIP probe 425 away from recognition site 150. This ensures that when complementary fragment 140 is generated, such as within the non-limiting example illustrated within FIG. 5(B), the completed double-stranded recognition site 150 and the surrounding bases are exact to the individual, and contain any mutations (e.g., SNPs) that are possessed by the individual and which can affect the binding affinity of one or more proteins. As before, complementary fragment 140 may not be extended such that MIP probe 425 is completely double-stranded, but is extended to the point where recognition site 150 is completely double-stranded (assuming the recognition site 150 is desirably double-stranded, such as when the binding protein has a palindromic recognition site). However, also as before, if the binding protein at issue is specific for RNA or single-stranded DNA (or such targets are of interest in the assay and the double-stranded target variants are not), then as with the embodiments described in association with FIGS. 1(A)-1(C) and 2(A)-2(C), complementary fragment 140 will not be generated.

FIG. 5(C) illustrates, as did FIGS. 1(C) and 2(C), a non-limiting example of subsequent binding of a binding protein 160 to recognition site 150, and the use of a label 170 for use in determining the affinity of binding protein 160 for the particular recognition site 150. As with the comparison of the embodiments for FIG. 2(A)-2(C) relative to FIG. 1(A)-1(C), this step of the assay as depicted within FIG. 5(C) is substantially similar in many respects.

The use of a MIP approach, according to the embodiments described in association with, for instance, the non-limiting examples within FIG. 2(A)-2(C) or 4(A)-4(D) and 5(A)-5(C), provides several additional advantages over embodiments such as those described in association with FIG. 1(A)-1(C). For instance, the use of MIP technology allows capture of regions of interest with higher specificity than can often be obtained with the use of a single capture oligonucleotide 120 alone as depicted in the non-limiting example within FIG. 1(A)-1(C). It is well known that many binding proteins are specific for sequences that occur multiple times throughout the genome, RNA transcripts, etc. of interest, and also that certain binding proteins possess at least a certain level of general affinity for multiple different DNA or RNA sequences. Thus, depending on the assay configuration, it can be difficult to ensure that the assay is measuring the affinity of a binding protein for a recognition site 150 within a particular location of interest within the genome, RNA transcripts, etc. that at issue within the assay. Embodiments which do not utilize a MIP approach within the overall assay, such as those embodiments illustrated within the non-limiting example of FIG. 1(A)-1(C), can compensate through a variety of solutions, such as, for example, use of unique sequences (and in some embodiments, sequences which are unique and conserved) within target fragment 130 to hybridize with the capture oligonucleotides 120.

The use of MIP technology within an assay, however, such as within embodiments illustrated within the non-limiting examples of FIGS. 2(A)-2(C), 3, 4(A)-4(D) and 5(A)-5(C), can provide substantial benefits (in terms of ease of assay design and customization, implementation, accuracy, precision, and consistency) to ensure that the binding protein affinity portion of the assay is measuring the affinity of the binding proteins for the recognition sites 150 of actual interest, and not that of recognition sites possessing the same or a similar recognition sequence that occur elsewhere in the genome, in RNA transcripts not of interest to the particular assay, etc. These benefits are largely provided by the inherent nature of the MIP probe structure in that two separate regions of the probe are required to cooperatively hybridize with the target nucleic acid at issue, which results in a corresponding increase in specificity in addition to an increased melting temperature ($T_m$) relative to a single region of hybridization, as well as providing more rapid hybridization kinetics. Moreover, the ability to require two separate regions for hybridization provides greater flexibility (compared to the use of a single capture oligonucleotide 120) in designing the probes for an assay that will capture the recognition site 150 within the target fragment 130 of interest, and not merely a recognition site 150 that is present within some other sequence within the sample (with this other sequence possessing some level of complementarity with capture oligonucleotide 120 such it hybridizes to a certain degree with capture oligonucleotide 120). As discussed earlier, the first and second genomic homology regions 330 and 335 can be designed to hybridize to the relevant target fragment 130 around the recognition site 150 of interest, thus allowing the gap fill portion of the reaction to add complementary bases and ensure that the resulting MIP probes (e.g., MIP probe 425) contain any mutations of the particular individual that provided the sample (e.g., SNPs, insertions, deletions, indels) within the combined genomic homology region 380. In turn, this ensures that any effects of the mutations will affect the results of the binding protein affinity portion of the assay.

Furthermore, other aspects of MIP technology facilitate the ease of use in the specific capture and downstream use of the precise recognition site 150 of interest. For instance, an in-solution use of MIP probes, such as the non-limiting example depicted within FIG. 4(A)-4(D), is utilized in many embodiments to selectively enrich the sample for the target fragments 130 containing the recognition sites 150 of interest. After addition of the MIP probes and their circularization, the non-circularized MIP probes and single-stranded nucleic acids of the sample can be removed (e.g., with an exonuclease treatment that does not degrade the circularized MIP probes). Combined with amplification of the circularized MIP probes (e.g., after linearization and use of PCR primer binding sites, or through rolling circle replication), the MIP approach thus greatly facilitates the introduction of nucleic acids to the array(s) of capture oligonucleotides 120 a nucleic acid sample that contains an amplified amount of the desired target fragments 130 of interest while containing a non-existent or minimal amount of undesired nucleic acids.

MIP technology also facilitates other aspects of the binding protein affinity portion of the assay. For example, use of a unique tag sequence 360 within MIP probe 410 (and which is present within MIP probe 425, or at least the complement of tag sequence 360) allows for hybridization of MIP probe 410 at a specific location within a tag microarray which possesses capture oligonucleotides 120 with an appropriately complementary sequence such that they hybridize with the tag sequence 360 of MIP probes 425. Incorporation of a different tag sequence within each MIP probe 410 allows that unique tag sequence 360 to accordingly denote the particular location of the recognition site 150. Thus, while a particular recognition sequence of a recognition site 150 may occur dozens, hundreds or thousands of times in a particular nucleic acid sample, the use of unique tag sequences 360 within a MIP approach facilitates the binding affinity of the protein(s) at issue to be precisely tested against the particular recognition site 150 of interest, and not merely other occurrences of the recognition sequence. This approach can thus be utilized to test a variety of recognition sites 150, all of which may have the same recognition sequence and which are binding targets for the same or similar binding proteins, within a single assay while facilitating the differentiation of one recognition site 150 and its source location within the genome, RNA transcript, etc. from another recognition site 150 with the same recognition sequence by simply having capture oligonucleotides 120 for different unique tag sequences 360 within different features of the microarray, attached to different distinguishable beads, or through other methods known in the art.

Many of the variations disclosed herein are desirably embodied within an assortment of kits. For example, kits are envisioned containing one or more substrates 110 with attached capture oligonucleotides 120. Many kit embodiments will additionally contain the necessary reagents for preparing a sample of nucleic acids for use with the capture oligonucleotides 120 (e.g., for amplification, purification, fragmentation, etc.). Furthermore, certain kit embodiments will also comprise binding proteins for use within the assay and/or the reagents necessary for in vitro translation of the binding proteins of interest (e.g., to create binding proteins of interest that are produced from the mRNA of the individual that provided the sample to ensure that any relevant mutations from the individual are accounted for within the binding protein affinity assay), and any associated molecules necessary for the assay (e.g., a cofactor necessary for the binding protein at issue to bind to its recognition site 150). Various kit embodiments will additionally comprise one or more labels of one or more types for use with the binding proteins and/or nucleic acids at issue within the assay, and may include, for example, various fluorescent labels, radioisotopes, and any necessary components for their use (e.g., antibodies, biotin). Kits will often additionally comprise any other reagents for the relevant assay. For instance, for embodiments which utilize MIP technology (e.g., in creating MIP probes 425 for use in the binding protein affinity assay as illustrated within the non-limiting example of FIGS. 4(A)-4(D) and 5(A)-5(C)), the kits will additionally comprise the MIP probes, enzymes, nucleotides, and other components necessary to conduct the MIP portion of the assay as well.

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

What is claimed is:

1. A method for measuring an affinity level of one or more binding proteins for one or more recognition sites, the method comprising:
    hybridizing one or more target nucleic acids to one or more probes, which probes each comprise a first homology region and a second homology region, wherein the first homology region hybridizes to a first region of a target nucleic acid, wherein the second homology region hybridizes to a second region of the same target nucleic acid, and wherein the first and second homology regions hybridize to the same target nucleic acid so that a gap of one or more bases separates the probe first and second homology regions;
    enzymatically extending one or more hybridized probes from the first or second homology region across the gap to synthesize a complementary nucleic acid, thereby creating a recognition site for a binding protein;
    introducing one or more putative binding proteins to the recognition site; and,
    measuring an affinity level of the one or more putative binding proteins for the recognition site.

2. The method of claim 1, wherein the recognition site comprises one or more mutations selected from the group consisting of: a single nucleotide polymorphism (SNP), an insertion, a deletion, and an inversion.

3. The method of claim 1, further comprising ligating a 3' end of the extended complementary nucleic acid to a 5' end of the hybridized probe.

4. The method of claim 3, wherein said ligating circularizes the probe, and wherein the probe comprises a cleavage site.

5. The method of claim 4, further comprising linearizing the circularized probe by cleaving the probe at the cleavage site.

6. The method of claim 1, wherein the one or more probes are attached to a substrate.

7. The method of claim 6, wherein a plurality of different probes are attached to the substrate at different substrate regions.

8. The method of claim 1, wherein the one or more probes comprise one or more polymerase chain reaction (PCR) primer binding sites.

9. The method of claim 8, further comprising amplifying the probe by PCR.

10. The method of claim 1, wherein the one or more putative binding proteins are produced through in vitro translation using RNA from an individual organism.

11. The method of claim 1, wherein the one or more putative binding proteins each comprise a detectable label.

12. The method of claim 11, wherein two or more of the putative binding proteins are different proteins and comprise distinguishable labels.

13. The method of claim 1, wherein said measuring the affinity level comprises quantitating the one or more binding proteins bound to the recognition site.

14. The method of claim 1, wherein said measuring the affinity level comprises an absolute quantification of one or more labels associated with the one or more binding proteins.

15. The method of claim 1, wherein measuring the affinity level comprises a relative quantification of one or more labels associated with two or more different binding proteins.

* * * * *